United States Patent
Ooms et al.

(10) Patent No.: US 8,022,240 B2
(45) Date of Patent: Sep. 20, 2011

(54) PROCESSES FOR PURIFYING DIARYL CARBONATES

(75) Inventors: Pieter Ooms, Krefeld (DE); Johann Rechner, Kempen (DE); Matthias Böhm, Leverkusen (DE); Andre Düx, Brühl (DE); Kaspar Hallenberger, Leverkusen (DE); Georg Ronge, Düsseldorf (DE); Johan Vanden Eynde, Zwijnaarde (BE)

(73) Assignee: Bayer MaterialScience AG, Leverkusen (DE)

( * ) Notice: Subject to any disclaimer, the term of this patent is extended or adjusted under 35 U.S.C. 154(b) by 177 days.

(21) Appl. No.: 12/274,776

(22) Filed: Nov. 20, 2008

(65) Prior Publication Data

US 2009/0137832 A1    May 28, 2009

(30) Foreign Application Priority Data

Nov. 20, 2007   (DE) .......................... 10 2007 055 266

(51) Int. Cl.
*C07C 67/02*   (2006.01)
(52) U.S. Cl. ....................................................... 558/274
(58) Field of Classification Search ................... 558/274
See application file for complete search history.

(56) References Cited

U.S. PATENT DOCUMENTS

| | | | |
|---|---|---|---|
| 5,334,742 A * | 8/1994 | Schon et al. | .................. 558/274 |
| 5,734,004 A | 3/1998 | Kuhling et al. | |
| 2007/0260084 A1 | 11/2007 | Fukuoka et al. | |

FOREIGN PATENT DOCUMENTS

| | | |
|---|---|---|
| DE | 3302525 A1 | 7/1984 |
| EP | 0122367 | 10/1984 |
| EP | 0784048 A1 | 7/1997 |
| EP | 1803704 A1 | 7/2007 |
| JP | 3291257 A | 12/1991 |

\* cited by examiner

*Primary Examiner* — Rebecca Anderson
*Assistant Examiner* — Samantha Shterengarts
(74) *Attorney, Agent, or Firm* — Connolly Bove Lodge & Hutz LLP

(57) ABSTRACT

Processes comprising: transesterifying a dialkyl carbonate and an aromatic hydroxyl compound in the presence of a transesterification catalyst to provide a diaryl carbonate product comprising the transesterification catalyst as an impurity; subjecting the diaryl carbonate product to distillation in a first distillation column having an upper part and a lower part, wherein the upper part comprises a rectifying section and the lower part comprises a stripping section; and withdrawing a first sidestream from the first distillation column, wherein the first sidestream comprises a purified diaryl carbonate.

18 Claims, 10 Drawing Sheets

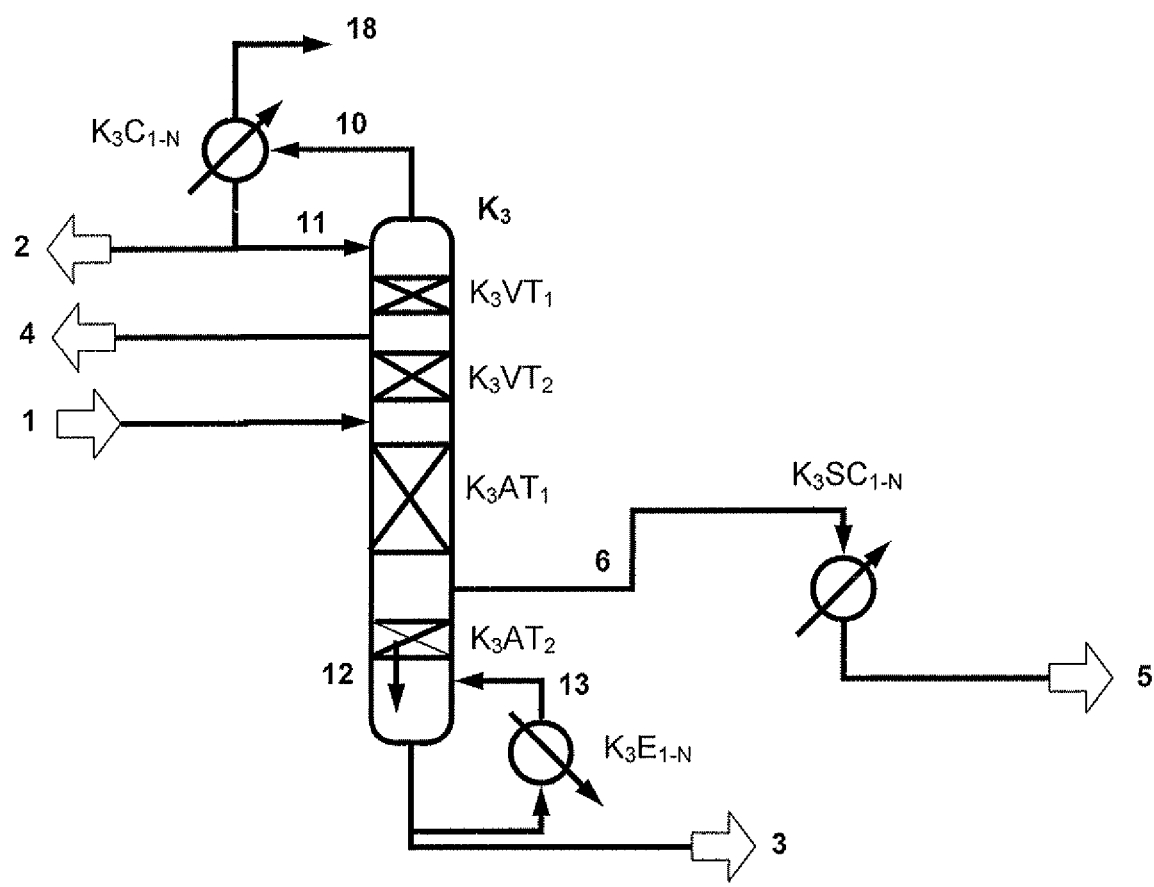
Fig. 1.1

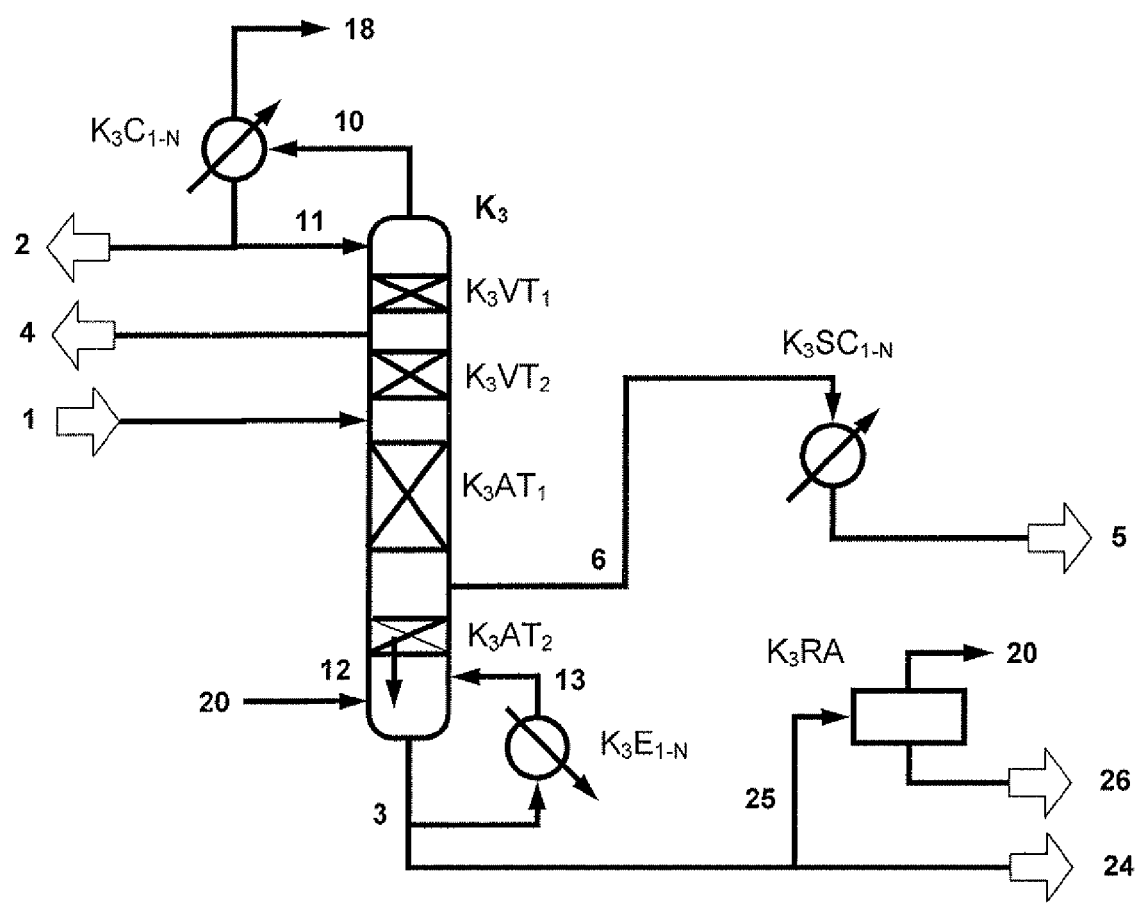
Fig. 1.2

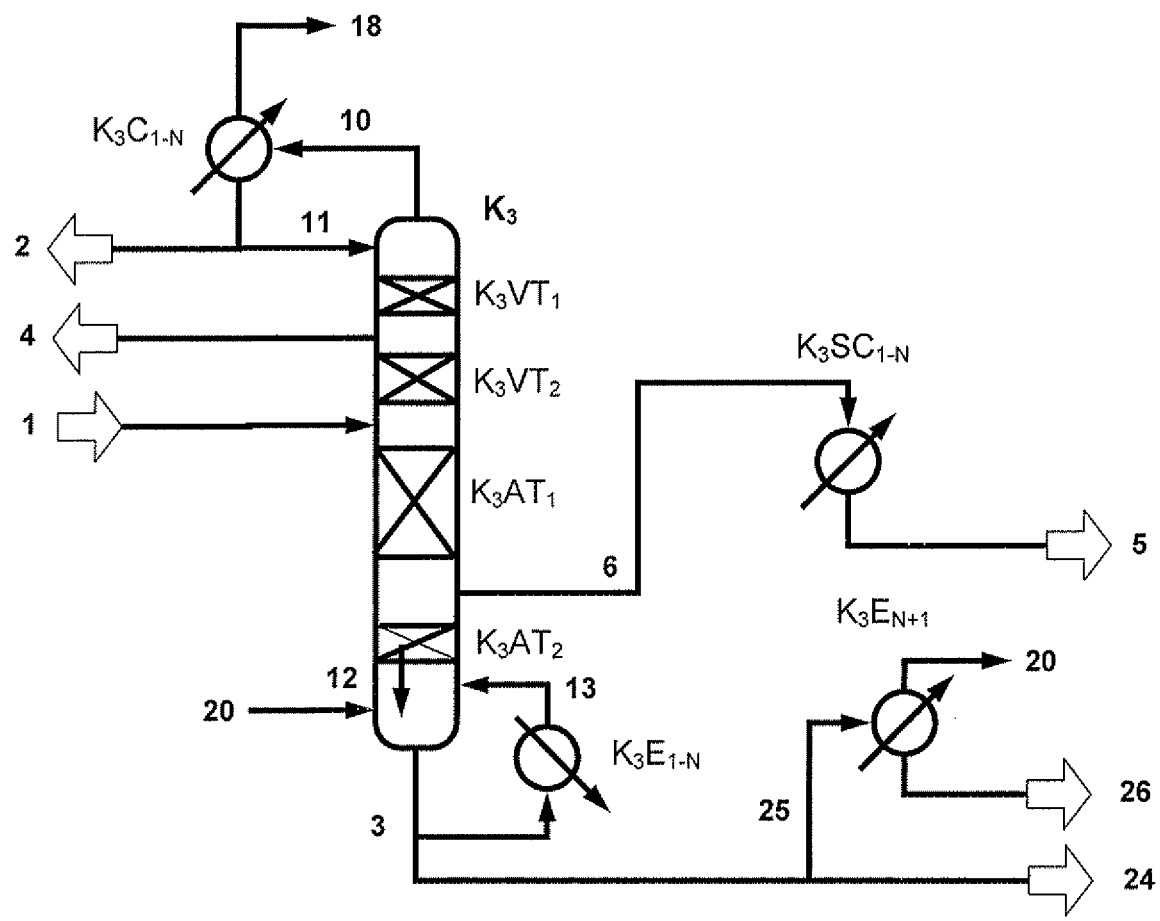
Fig. 1.3

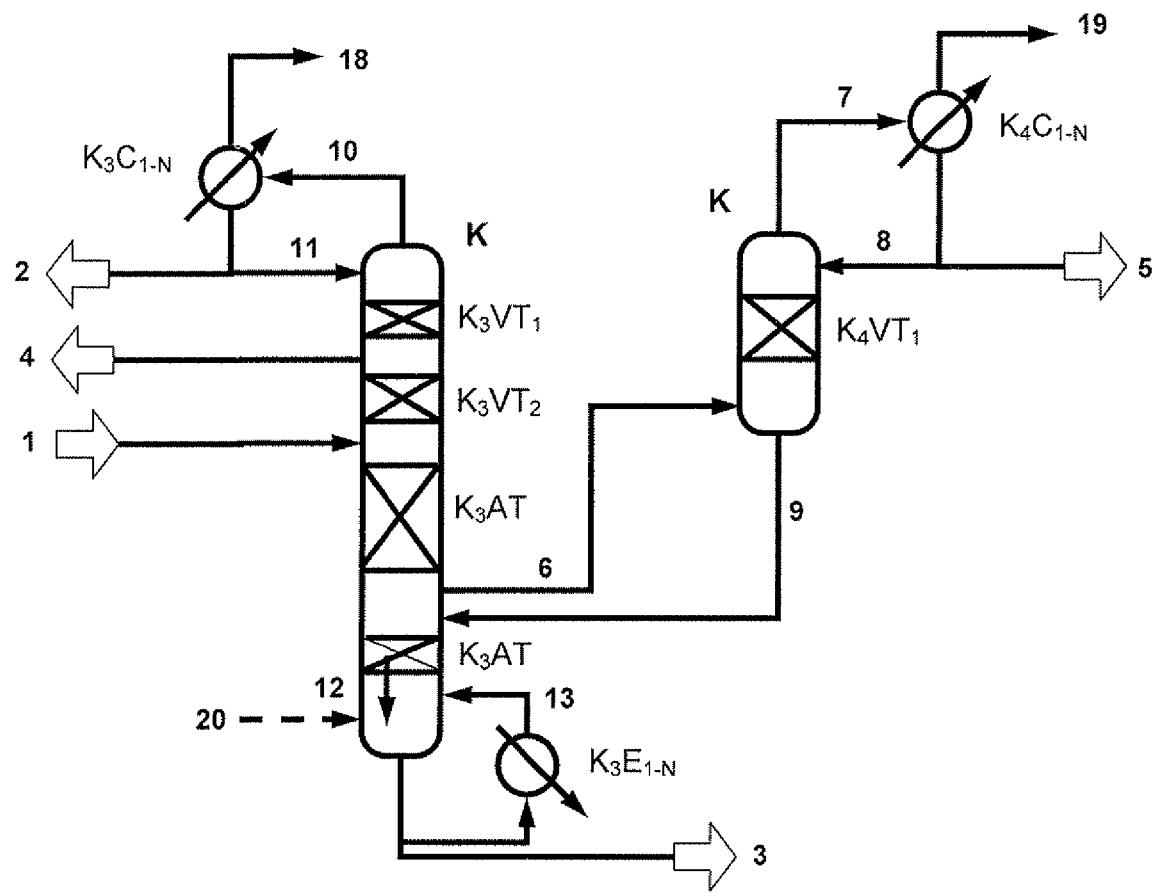
Fig. 2.1

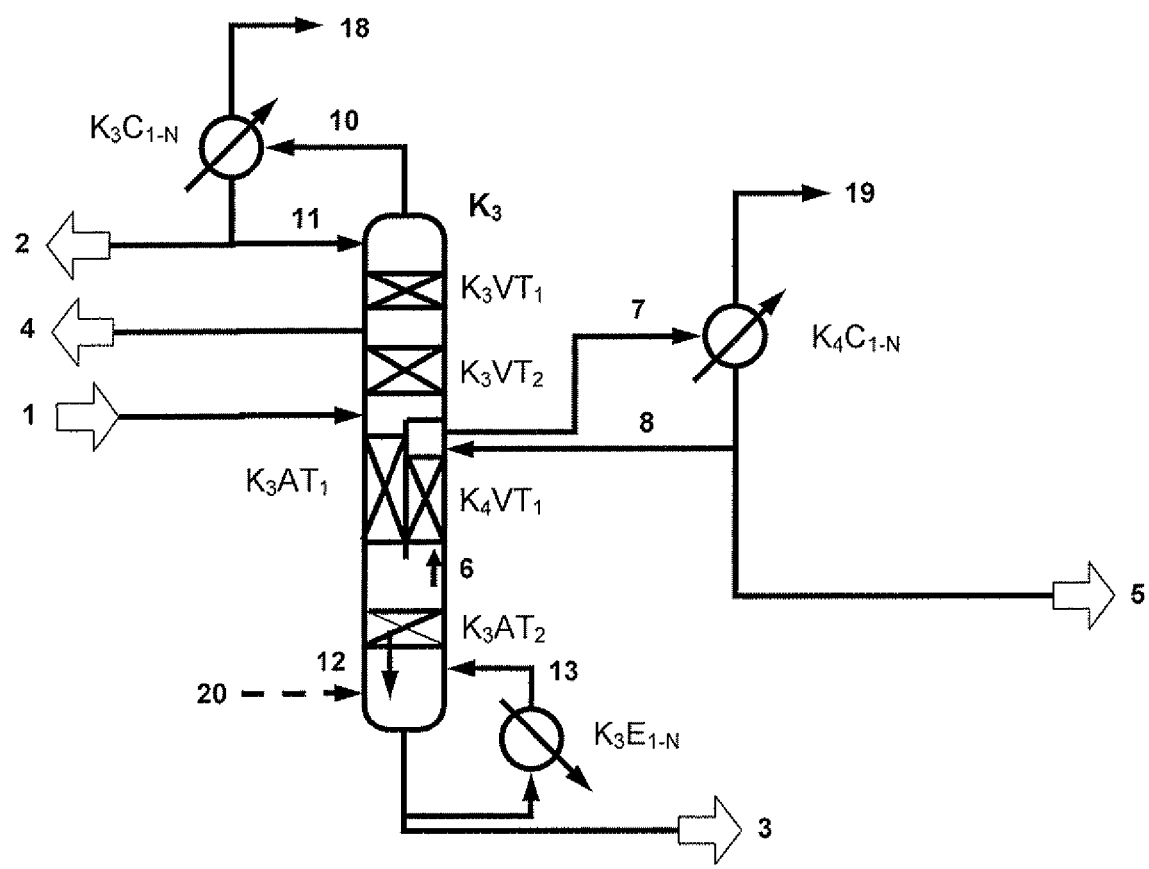
Fig. 2.2

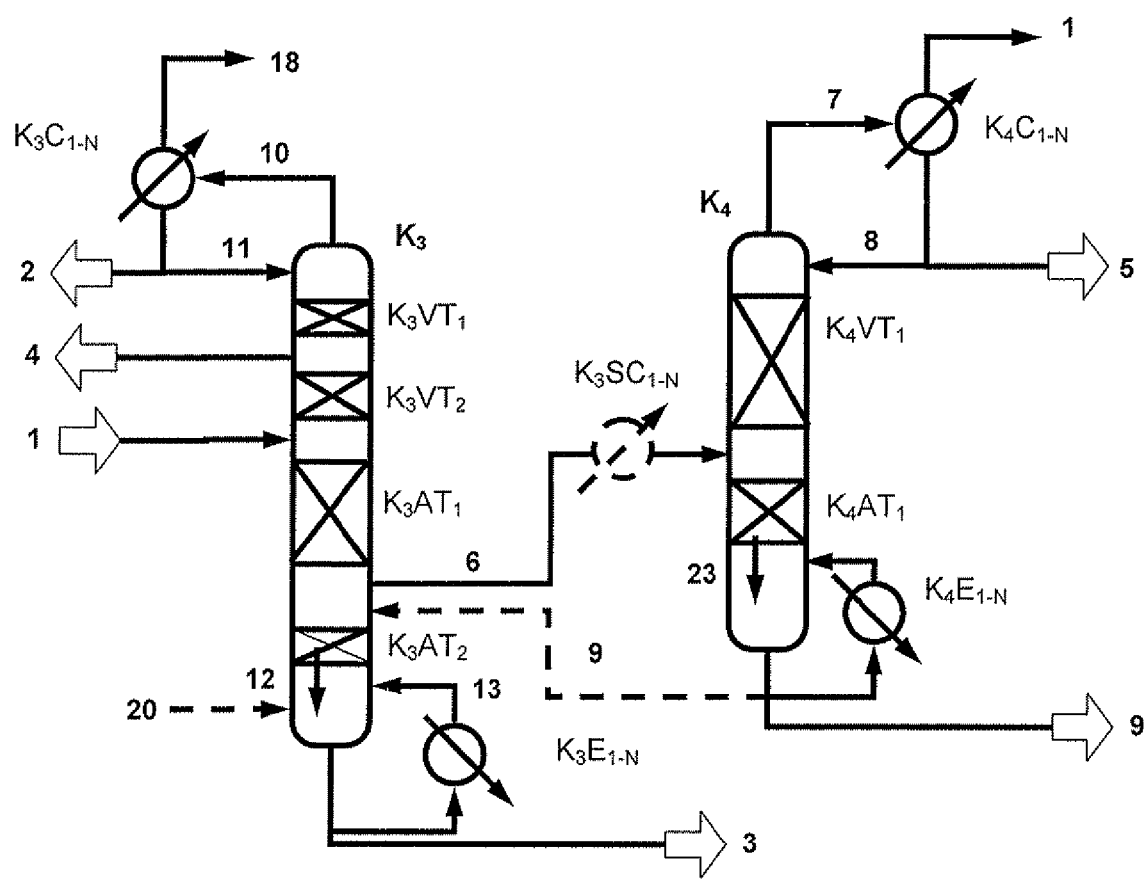
Fig. 2.3

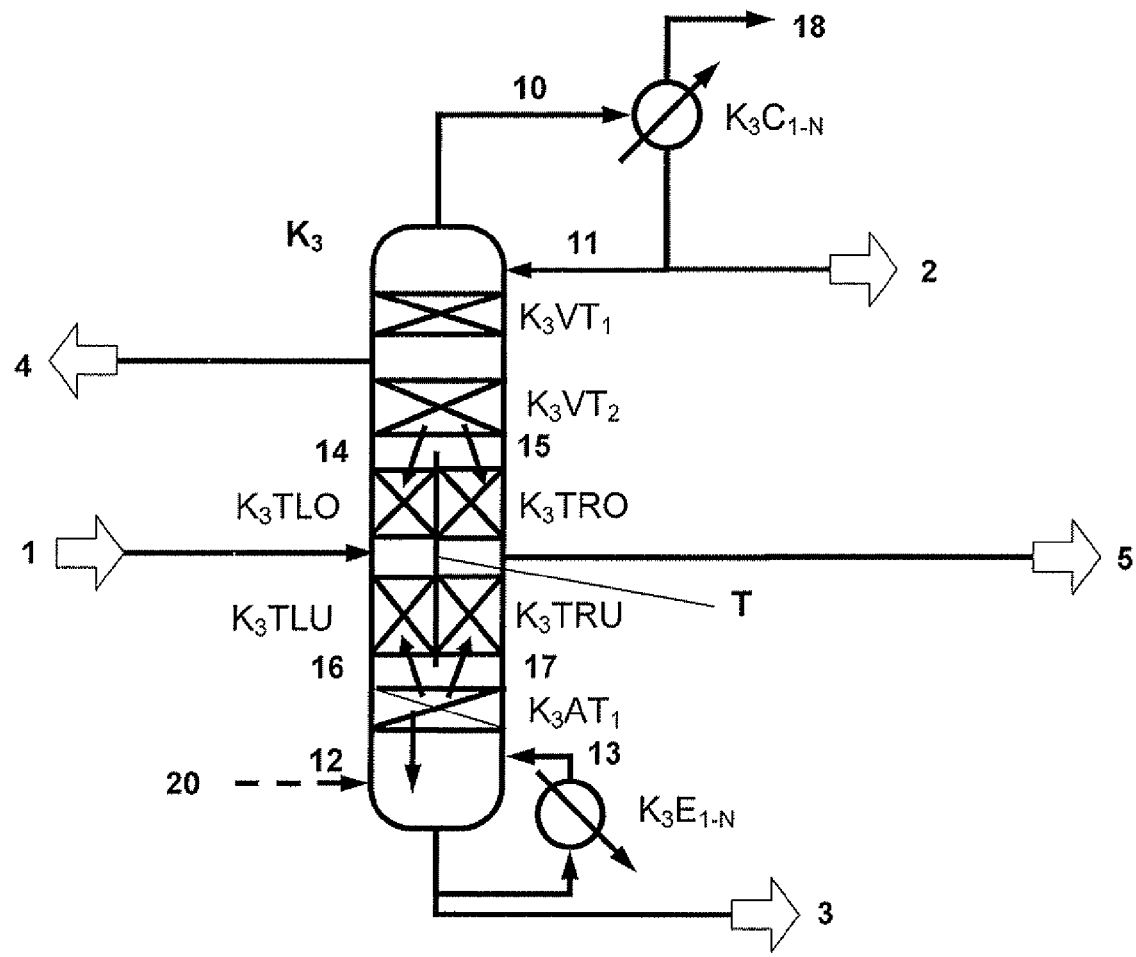
Fig. 3.1

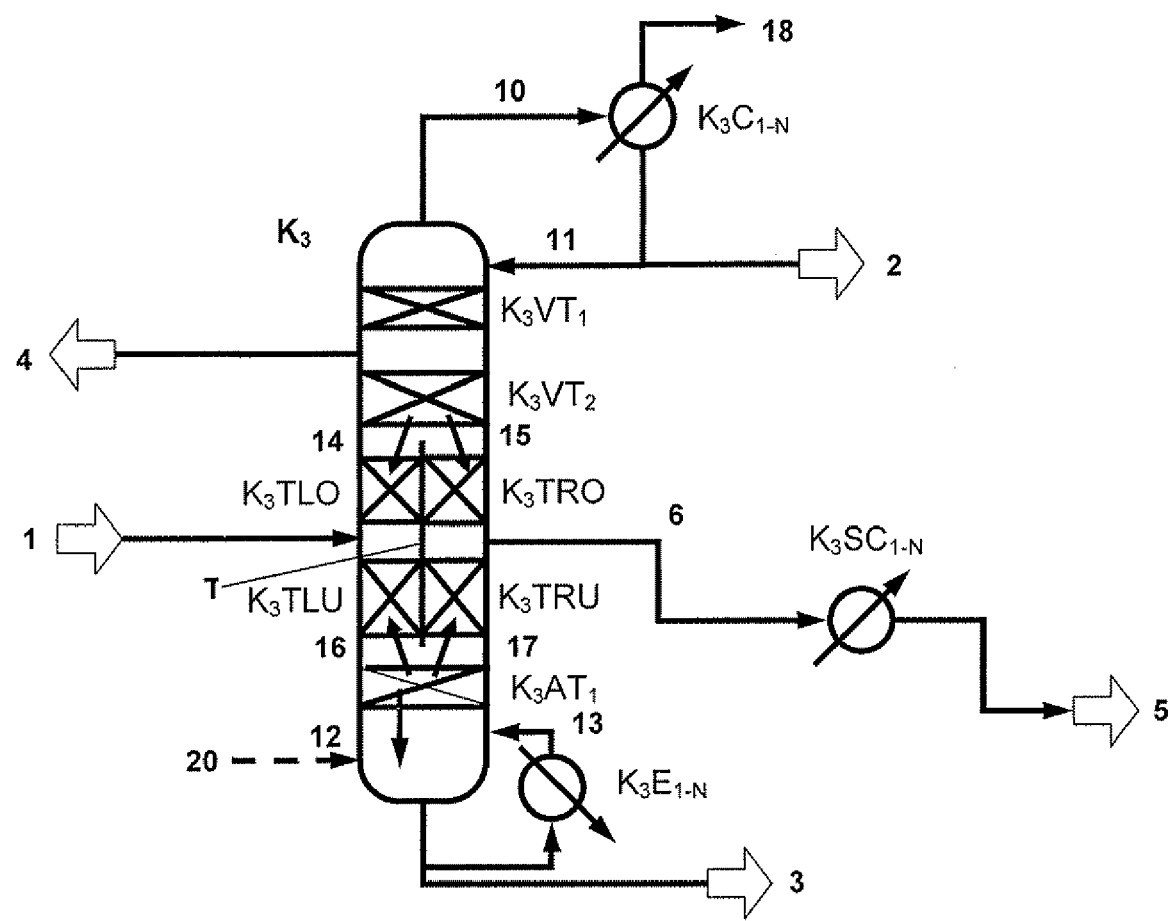
Fig. 3.2

PROCESSES FOR PURIFYING DIARYL CARBONATES

BACKGROUND OF THE INVENTION

The purification of diaryl carbonates is of great significance owing to the high requirements on the purity thereof for the preparation of qualitatively high-value polycarbonates by melt transesterification, Diaryl carbonates prepared from transesterification of an aromatic hydroxyl compound with an alkyl carbonate may comprise both high-boiling and medium-boiling secondary components, and also catalyst residues, as impurities. High-boiling components—often also referred to as high boilers—in the context of such preparation processes are those whose boiling points are above that of the diaryl carbonate. Medium-boiling components—often also referred to as intermediate boilers—in the context of such preparation processes are those whose boiling points are between that of the diaryl carbonate and that of the alkyl aryl carbonate which can be formed as a by-product during the preparation of the diaryl carbonate. All of these impurities can lead to considerable qualitative impairment of the polycarbonates to be prepared and have to be removed by appropriate purification before the further use of the diaryl carbonates.

International Patent Publication No. WO 2004/113264, the entire contents of which are hereby incorporated herein by reference, describes a process for recovering a product stream from a waste stream in the preparation of diaryl carbonate. Also described is a refining of the diaryl carbonate which has been prepared in a reaction using three reaction columns, and which is carried out in three stages including catalyst removal, low boiler removal and high boiler removal. Both in the first and in the latter step, the diaryl carbonate is removed as the top product. The process described is not only exceptionally complex in apparatus terms, but also energetically unfavorable owing to the removal of the diaryl carbonate both in the first stage and in the third stage as the top product. In addition, the quality of the diaryl carbonate thus prepared is very poor at 99.5% by weight and is unsuitable for the preparation of qualitatively high-value polycarbonate.

European Patent Publication No. EP 1 760 069 A, the entire contents of which are hereby incorporated herein by reference, describes a process for preparing diaryl carbonates, in which, after the transesterification of an aromatic hydroxyl compound with an alkyl carbonate, a mixture is obtained which, as well as diaryl carbonate, comprises an aromatic carbonate ether as an impurity among other impurities. The latter is removed in a subsequent step in order to obtain a high-purity diaryl carbonate. The significantly more complex removal of high-boiling secondary components, which would lead to qualitative impairment of the target products polycarbonates), is, however, not described.

European Patent Publication Nos. EP 1 783 112 A1, EP 1 787 977 A1, EP 1 801 095 A1 and EP 1 787 976 A1, the entire contents of each of which are hereby incorporated herein by reference, describe a process consisting of at least two stages for purifying diaryl carbonate, especially diphenyl carbonate, in which the high-boiling components and the catalyst are first removed after the reaction. The distillate obtained in this high boiler removal is separated into three fractions in a second distillation column, diaryl carbonate being withdrawn in the sidestream. However, a disadvantage of this process is that the high-boiling components are removed in the first step, since this is energetically unfavorable.

European Patent Publication No. EP 784 048 A, the entire contents of which are hereby incorporated herein by reference, describes a process for purifying diaryl carbonates, in which a distillation is carried out at a bottom temperature greater than 150° C. and the product withdrawal of the purified diaryl carbonate is effected in the sidestream of the column. The diaryl carbonates to be purified can be prepared either by reaction of carbonyl halides with aromatic hydroxyl compounds or by transesterification of aromatic hydroxyl compounds with dimethyl carbonate. Although the process described enables diaryl carbonates to be freed very substantially of high boilers, for example phenyl salicylate, nowhere is the presence of troublesome catalyst residues or intermediate boilers or a means for their removal described. Especially the presence of significant amounts of catalyst residues can, however, influence a distillative purification, since this accelerates the side reaction of diaryl carbonate to give phenyl salicylate and hence promotes the enrichment thereof in the bottom of the column. Therefore, the process described in EP 784 048 A is not immediately suitable for such a purification in the presence of catalyst residues and/or intermediate boilers.

BRIEF SUMMARY OF THE INVENTION

The present invention relates, in general, to processes for purifying diaryl carbonates. More particularly, the present invention relates to processes for purifying diaryl carbonates in which catalyst residues and high-boiling secondary components and if appropriate also medium-boiling secondary components are removed as impurities with a design which is very simple in apparatus terms and energetically favorable.

It has now surprisingly been found that the distillative purification of diaryl carbonates can also be performed with a low level of apparatus complexity and energy demands when the diaryl carbonates to be purified comprise catalyst residues and high-boiling secondary components, and possibly also medium-boiling secondary components, as impurities. At the same time, the waste obtained in the distillation can preferably even be utilized energetically.

The present invention provides processes for purifying diaryl carbonates in at least one distillation column comprising at least one rectifying section in the upper part of the column and at least one stripping section in the lower part of the column, characterized in that:

the diaryl carbonate to be purified has been prepared by transesterification from at least one dialkyl carbonate and at least one aromatic hydroxyl compound in the presence of at least one transesterification catalyst and comprises catalyst from the preparation of the diaryl carbonate as an impurity, and the purified diaryl carbonate is withdrawn in the sidestream of the first distillation column.

One embodiment of the present invention includes a process comprising: transesterifying a dialkyl carbonate and an aromatic hydroxyl compound in the presence of a transesterification catalyst to provide a diaryl carbonate product comprising the transesterification catalyst as an impurity; subjecting the diaryl carbonate product to distillation in a first distillation column having an upper part and a lower part, wherein the upper part comprises a rectifying section and the lower part comprises a stripping section; and withdrawing a first sidestream from the first distillation column, wherein the first sidestream comprises a purified diaryl carbonate.

Another embodiment of the present invention includes a process comprising: transesterifying a dialkyl carbonate and an aromatic hydroxyl compound in the presence of a transesterification catalyst to provide a diaryl carbonate product comprising the transesterification catalyst as an impurity; subjecting the diaryl carbonate product to distillation in a first dividing wall distillation column having an upper part, a lower part, and a dividing wall section, wherein the upper part comprises a rectifying section and the lower part comprises a stripping section; and withdrawing a first sidestream from the first distillation column, wherein the first sidestream comprises a purified diaryl carbonate, wherein the dividing wall section comprises a dividing wall, a feed side and a withdrawal side; wherein the feed side comprises an upper feed side section and a lower feed side section, and the withdrawal side comprises an upper withdrawal side section and a lower withdrawal side section; and wherein the diaryl carbonate product is fed to the first distillation column between the upper and lower feed side sections and the first sidestream is withdrawn from the first distillation column between the upper and lower withdrawal sections.

BRIEF DESCRIPTION OF THE SEVERAL VIEWS OF THE DRAWING

The foregoing summary, as well as the following detailed description of the invention, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings:

FIG. 1.1 is a process diagram of a purification of diaryl carbonate in a distillation column in accordance with an embodiment of the present invention;

FIG. 1.2 is a process diagram of a purification of diaryl carbonate in a distillation column with additional residue concentration in accordance with an embodiment of the present invention;

FIG. 1.3 is a process diagram of a purification of diaryl carbonate in a distillation column with an additional residue concentration in the form of an evaporator in accordance with an embodiment of the present invention;

FIG. 2.1 is a process diagram of a purification of diaryl carbonate in a distillation column with additional external sidestream column which is designed as a rectifying section in accordance with an embodiment of the present invention;

FIG. 2.2 is a process diagram of a purification of diaryl carbonate in a distillation column with additional integrated sidestream column which is designed as a rectifying section in accordance with an embodiment of the present invention;

FIG. 2.3 is a process diagram of a purification of diaryl carbonate in a distillation column with additional external sidestream column which has a rectifying section and a stripping section in accordance with an embodiment of the present invention;

FIG. 3.1 is a process diagram of a purification of diaryl carbonate in a dividing wall column with liquid sidestream withdrawal of the purified diaryl carbonate in accordance with an embodiment of the present invention;

FIG. 3.2 is a process diagram of a purification of diaryl carbonate in a dividing wall column with vaporous sidestream withdrawal of the purified diaryl carbonate in accordance with an embodiment of the present invention;

DETAILED DESCRIPTION OF THE INVENTION

Figure 4:
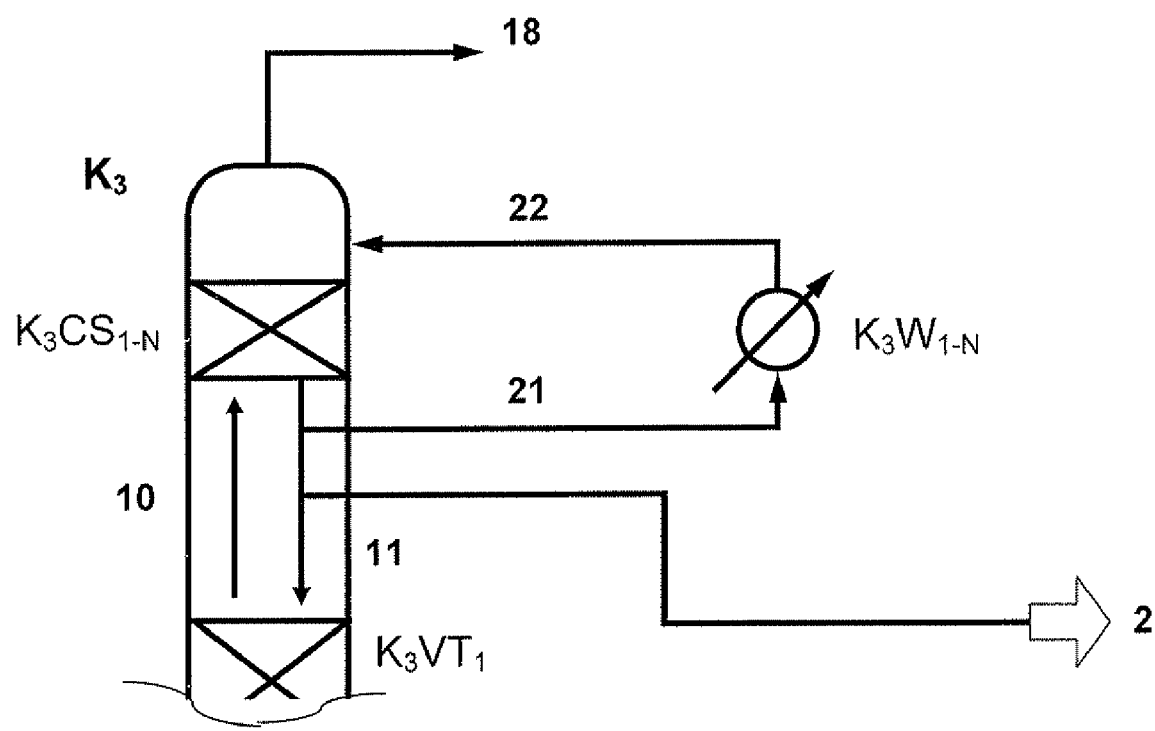
FIG. 4 is a process diagram of a section of the condensation at the top of a distillation or dividing wall column in one or more additional column section(s) with a condensate cooled in an external circuit in accordance with an embodiment of the present invention.

As used herein, the singular terms "a" and "the" are synonymous and used interchangeably with "one or more" and "at least one," unless the language and/or context clearly indicates otherwise. Accordingly, for example, reference to "a dialkyl carbonate" herein or in the appended claims can refer to a single dialkyl carbonate or more than one dialkyl carbonate. Additionally, all numerical values, unless otherwise specifically noted, are understood to be modified by the word "about."

Diaryl carbonates which can be purified in the context of the invention include those of the general formula (I)

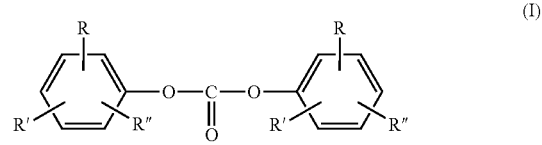

where R, R' and R" are each independently H, linear or branched, optionally substituted $C_1$-$C_{34}$-alkyl, preferably $C_1$-$C_6$-alkyl, more preferably $C_1$-$C_4$-alkyl, $C_1$-$C_{34}$-alkoxy, preferably $C_1$-$C_6$-alkoxy, more preferably $C_1$-$C_4$-alkoxy, $C_5$-$C_{34}$-cycloalkyl, $C_7$-$C_{34}$-alkylaryl, $C_6$-$C_{34}$-aryl or a halogen radical, preferably a chlorine radical, and R, R' and R" on the two sides of the formula (I) may be the same or different. R may also be —COO—R'" where R'" is H, branched or unbranched $C_1$-$C_{34}$ alkyl, preferably $C_1$-$C_6$-alkyl, more preferably $C_1$-$C_4$-alkyl, $C_1$-$C_{34}$-alkoxy, preferably $C_1$-$C_6$-alkoxy, more preferably $C_1$-$C_4$-alkoxy, $C_5$-$C_{34}$-cycloalkyl, $C_7$-$C_{34}$-alkylaryl or $C_6$-$C_{34}$-aryl. Preferably, R, R' and R" on the two sides of the formula (I) are the same. Most preferably, R, R' and R" are each H.

Diaryl carbonates of the general formula (I) include, for example: diphenyl carbonate, methylphenyl phenyl carbonates and di(methylphenyl) carbonates, also as a mixture, where the position of the methyl group on the phenyl rings may be as desired, and also dimethylphenyl phenyl carbonates and di(dimethylphenyl) carbonates, also as a mixture, where the position of the methyl groups on the phenyl rings may be as desired, chlorophenyl phenyl carbonates and di(chlorophenyl) carbonates, where the position of the methyl group on the phenyl rings may be as desired, 4-ethylphenyl phenyl carbonate, di(4-ethylphenyl) carbonate, 4-n-propylphenyl phenyl carbonate, di(4-n-propylphenyl) carbonate, 4-isopropylphenyl phenyl carbonate, di(4-isopropylphenyl) carbonate, 4-n-butylphenyl phenyl carbonate, di(4-n-butylphenyl) carbonate, 4-isobutylphenyl phenyl carbonate, di(4-isobutylphenyl) carbonate, 4-tert-butylphenyl phenyl carbonate, di(4-tert-butylphenyl) carbonate, 4-n-pentylphenyl phenyl carbonate, di(4-n-pentylphenyl) carbonate, 4-n-hexylphenyl phenyl carbonate, di(4-n-hexylphenyl) carbonate, 4-isooctylphenyl phenyl carbonate, di(4-isooctylphenyl) carbonate, 4-n-nonylphenyl phenyl carbonate, di(4-n-nonylphenyl) carbonate, 4-cyclohexylphenyl phenyl carbonate, di(4-cyclohexylphenyl) carbonate, 4-(1-methyl-1-phenylethyl)phenyl phenyl carbonate, di[4-(1-methyl-1-phenylethyl)phenyl]carbonate, biphenyl-4-yl phenyl carbonate, di(biphenyl-4-yl) carbonate, 1-naphthyl phenyl carbonate, 2-naphthyl phenyl carbonate, di(1-naphthyl) carbonate, di(2-naphthyl) carbonate, 4-(1-naphthyl)phenyl phenyl carbonate, 4-(2-naphthyl)phenyl phenyl carbonate, di[4-(1-naphthyl)phenyl]carbonate, di[4-(2-naphthyl)phenyl]carbonate, 4-phenoxyphenyl phenyl carbonate, di(4-phenoxyphenyl) carbonate, 3-pentadecylphenyl phenyl carbonate, di(3-pentadecylphenyl) carbonate, 4-tritylphenyl phenyl carbonate, di(4-tritylphenyl) carbonate, (methyl salicylate) phenyl carbonate, di(methyl salicylate) carbonate, (ethyl salicylate) phenyl carbonate, di(ethyl salicylate) carbonate, (n-propyl salicylate) phenyl carbonate, di(n-propyl salicylate) carbonate, (isopropyl salicylate) phenyl carbonate, di(isopropyl salicylate) carbonate, (n-butyl salicylate) phenyl carbonate, di(n-butyl salicylate) carbonate, (isobutyl salicylate) phenyl carbonate, di(isobutyl salicylate) carbonate, (tert-butyl salicylate) phenyl carbonate, di(tert-butyl salicylate) carbonate, di(phenyl salicylate) carbonate and di(benzyl salicylate) carbonate.

Preferred diaryl carbonates include: diphenyl carbonate, 4-tert-butylphenyl phenyl carbonate, di(4-tert-butylphenyl) carbonate, biphenyl-4-yl phenyl carbonate, di(biphenyl-4-yl) carbonate, 4-(1-methyl-1-phenylethyl)phenyl phenyl carbonate and di[4-(1-methyl-1-phenylethyl)phenyl]carbonate. A particularly preferred diaryl carbonate is diphenyl carbonate.

In the context of the invention, dialkyl carbonates include those of the formula (II)

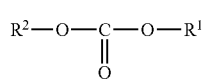

(II)

where $R^1$ and $R^2$ are each independently linear or branched, optionally substituted $C_1$-$C_{34}$-alkyl, preferably $C_1$-$C_6$-alkyl, more preferably $C_1$-$C_4$-alkyl. $R^1$ and $R^2$ may be the same or different. $R^1$ and $R^2$ are preferably the same.

Preferred dialkyl carbonates include dimethyl carbonate, diethyl carbonate, di(n-propyl) carbonate, di(isopropyl) carbonate, di(n-butyl) carbonate, di(sec-butyl) carbonate, di(tert-butyl) carbonate or dihexyl carbonate. Particular preference is given to dimethyl carbonate or diethyl carbonate. Very particular preference is given to dimethyl carbonate.

In the context of the invention, aromatic hydroxyl compounds include those of the general formula (III)

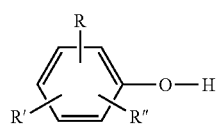

(III)

in which R, R' and R" may each independently be as defined for the general formula (I).

Such aromatic hydroxyl compounds include, for example: phenol, o-, m- or p-cresol, also as a mixture of the cresols, dimethylphenol, also as a mixture, where the position of the methyl groups on the phenol ring may be as desired, e.g. 2,4-, 2,6-, or 3,4-dimethylphenol, o-, m- or p-chlorophenol, o-, m- or p-ethylphenol, o-, m- or p-n-propylphenol, 4-isopropylphenol, 4-n-butylphenol, 4-isobutylphenol, 4-tert-butylphenol, 4-n-pentylphenol, 4-n-hexylphenol, 4-isooctylphenol, 4-n-nonylphenol, o-, m- or p-methoxyphenol, 4-cyclohexylphenol, 4-(1-methyl-1-phenylethyl)phenol, biphenyl-4-ol, 1-naphthol, 2-1-naphthol, 4-(1-naphthyl)phenol, 4-(2-naphthyl)phenol, 4-phenoxyphenol, 3-pentadecylphenol, 4-tritylphenol, methylsalicylic acid, ethylsalicylic acid, n-propylsalicylic acid, isopropylsalicylic acid, n-butylsalicylic acid, isobutylsalicylic acid, tert-butylsalicylic acid, phenylsalicylic acid and benzylsalicylic acid.

Preferred aromatic hydroxyl compounds include phenol, 4-tert-butylphenol, biphenyl-4-ol and 4-(1-methyl-1-phenylethyl)phenol. Particular preference is given to phenol.

Both the dialkyl carbonates specified above and the aromatic hydroxyl compounds are known to those skilled in the art and are commercially available or can be prepared by processes likewise known to those skilled in the art.

In the context of the invention, $C_1$-$C_4$-alkyl refers to, for example, methyl, ethyl, n-propyl, isopropyl, n-butyl, sec-butyl, tert-butyl; $C_1$-$C_6$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl; $C_1$-$C_{34}$-alkyl is additionally, for example, n-heptyl and n-octyl, pinacyl, adamantyl, the isomeric menthyls, n-nonyl, n-decyl, n-dodecyl, n-tridecyl, n-tetradecyl, n-hexadecyl or n-octadecyl. The same applies to the corresponding alkyl radical, for example in aralkyl or alkylaryl radicals. Alkylene radicals in the corresponding hydroxyalkyl or aralkyl or alkylaryl radicals are, for example, the alkylene radicals corresponding to the above alkyl radicals.

Aryl refers to a carbocyclic aromatic radical having 6 to 34 skeleton carbon atoms. The same applies to the aromatic moiety of an arylalkyl radical, also known as aralkyl radical, and also to aryl constituents of more complex groups, for example arylcarbonyl radicals.

Arylalkyl or aralkyl is in each case independently a straight-chain, cyclic, branched or unbranched alkyl radical as defined above, which may be mono-, poly- or per substituted by aryl radicals as defined above.

The above lists are illustrative and should not be understood as a limitation.

Transesterification catalysts for the preparation of the diaryl carbonates to be purified and to be removed therefrom as impurities may be transesterification catalysts known from the literature for the dialkyl carbonate-phenol transesterification, for example hydrides, oxides, hydroxides, alkoxides, amides and other salts of alkali metals and alkaline earth metals, such as those of lithium, sodium, potassium, rubidium, cesium, magnesium and calcium, preferably lithium, sodium, potassium, magnesium and calcium and more preferably lithium, sodium and potassium (cf for example, U.S. Pat. Nos. 3,642,858, 3,803,201 and European Patent Publication No. EP-A 1082, the entire contents of each of which are hereby incorporated by reference). Salts of the alkali metals and alkaline earth metals may also be those of organic or inorganic acids, such as those of acetic acid, propionic acid, butyric acid, benzoic acid, stearic acid, carbonic acid (carbonates or hydrogencarbonates), phosphoric acid, hydrocyanic acid, thiocyanic acid, boric acid, tin acid, $C_{14}$-stannoic acids or antimony acid. Preferred compounds of the alkali metals and alkaline earth metals are the oxides, hydroxides, alkoxides, acetates, propionates, benzoates, carbonates and hydrogencarbonates; particular preference is given to using hydroxides, alkoxides, acetates, benzoates or carbonates. The alkali metal or alkaline earth metal compounds mentioned are used preferably in amounts of 0.001 to 2% by weight, preferably of 0.005 to 0.9% by weight and more preferably of 0.01 to 0.5% by weight based on the weight of the reaction mixture to be converted.

Further catalysts usable in accordance with the invention are metal compounds such as $AlX_3$, $TiX_3$, $UX_4$, $TiX_4$, $VOX_3$, $VX_5$, $ZnX_2$, $FeX_3$, $PbX_2$ and $SnX_4$, in which X represents halogen, acetoxy, alkoxy or aryloxy radicals (DE-A 2 58 412). Particularly preferred catalysts usable in accordance with the invention are metal compounds such as $AlX_3$, $TiX_4$, $PbX_2$ and $SnX_4$, for example titanium tetrachloride, titanium tetramethoxide, titanium tetraphenoxide, titanium tetraethoxide, titanium tetraisopropoxide, titanium tetradodecoxide, tin tetraisooctoxide and aluminum triisopropoxide. Very particular preference is given to metal compounds $TiX_4$. The metal compounds mentioned are used preferably in amounts of 0.001 to 5% by weight, preferably of 0.005 to 5% by weight and more preferably of 0.01 to 5% by weight, based on the weight of the reaction mixture to be converted.

In the context of the invention, halogen is fluorine, chlorine or bromine, preferably fluorine or chlorine, more preferably chlorine.

Further catalysts usable in accordance with the invention are organotin compounds of the general formula $(R^{11})_{4-x}$—$Sn(Y)_x$ in which Y is an $OCOR^{12}$, OH or OR radical, where $R^{12}$ is $C_1$-$C_{12}$-alkyl, $C_6$-$C_{12}$-aryl or $C_7$-$C_{13}$-alkylaryl, $R^{11}$, independently of $R^{12}$, is as defined for $R^{12}$, and x is an integer from 1 to 3, dialkyltin compounds having 1 to 12 carbon atoms in the alkyl radical or bis(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctoxide, octyltin triisooctoxide, butylstannoic acid and octylstannoic acid, in amounts of 0.001 to 20% by weight (cf. EP 879, EP 880, EP 39 452, DE-A 34 45 555, JP 79/63023, the entire contents of each of which are hereby incorporated by reference), polymeric tin compounds of the formula —[—$RR^{11}Sn$—O—]— in which R and $R^{11}$ are each independently as defined above for $R^{12}$, for example poly[oxy(dibutylstannylene)], poly[oxy(dioctylstamylene)], poly[oxy(butylphenylstannylene)] and poly[oxy(diphenylstannylene)] (DE-A 34 45 552, the entire contents of which are hereby incorporated by reference), polymeric hydroxystannoxanes of the formula —[—RSn(OH)—O—]—, for example poly(ethylhydroxystannoxane), poly(butylhydroxystannoxane), poly(octylhydroxystannoxane), poly(undecylhydroxystannoxane) and poly(dodecylhydroxystannoxanes) in amounts of 0.001 to 20% by weight, preferably of 0.005 to 5% by weight, based on dialkyl carbonate (DE-A 40 06 520, the entire contents of which are hereby incorporated by reference). Further tin compounds usable in accordance with the invention are Sn(II) oxides of the general formula X—$R_2$Sn—O—$R_2$Sn—Y, in which X and Y are each independently OH, SCN, $OR^{13}$, $OCOR^{13}$ or halogen and R is alkyl, aryl, in which $R^{13}$ is as defined above for $R^{12}$ (EP 0 338 760, the entire contents of which are hereby incorporated by reference).

As further catalysts usable in accordance with the invention come lead compounds, optionally together with triorganophosphines, a chelate compound or an alkali metal halide, for example $Pb(OH)_2$-$2PbCO_3$, $Pb(OCO$—$CH_3)_2$, $Pb(OCO$—$CH_3)_2$.$2LiCl$, $Pb(OCO$—$CH_3)_2$.$2PPh_3$, in amounts of 0.001 to 1 mol, preferably of 0.005 to 0.25 mol, per mole of dialkyl carbonate (JP 57/176932, JP 01/093580, the entire contents of each of which are hereby incorporated by reference), and also other lead(II) and lead(IV) compounds, such as PbO, $PbO_2$, minimum, plumbites and plumbates (JP 01/093560), iron(III) acetate (JP 61/1 72 852, the entire contents of which are hereby incorporated by reference), and also copper salts and/or metal complexes, for example of alkali metals, zinc, titanium and iron (JP 89/005588, the entire contents of which are hereby incorporated by reference).

Preferred catalysts for the process according to the invention are the above-specified metal compounds $AlX_3$, $TiX_3$, $UX_4$, $TiX_4$, $VOX_3$, $VX_5$, $ZnX_2$, $FeX_3$, $PbX_2$ and $SnX_4$. Particular preference is given to $AlX_3$, $TiX_3$, $PbX_2$ and $SnX_4$, among which mention should be made by way of example of titanium tetrachloride, titanium tetramethoxide, titanium tetraphenoxide, titanium tetraethoxide, titanium tetraisopropoxide, titanium tetradodecoxide, tin tetraisooctoxide and aluminum triisopropoxide. Very particular preference is given to metal compounds $TiX_4$. Especially preferred are titanium tetramethoxide, titanium tetraphenoxide and titanium tetraethoxide.

In various preferred embodiments, the diaryl carbonate to be purified comprises compounds having a boiling point between that of the diaryl carbonate and the alkyl aryl carbonate formed as an intermediate during the preparation of the diaryl carbonate as an impurity, which are removed in a further sidestream of the first distillation column. This further sidestream withdrawal is effected in the first distillation column, preferably above the sidestream withdrawal for the diaryl carbonate.

Alkyl aryl carbonates formed as an intermediate during the preparation of the diaryl carbonate, in the context of the invention, are preferably those of the general formula (IV)

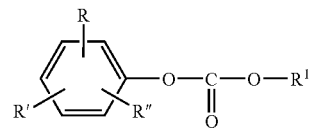

in which R, R' and R" may each be as defined for the general formula (I), and $R^1$ as defined for the general formula (II).

Preferred alkyl aryl carbonates are methyl phenyl carbonate, ethyl phenyl carbonate, propyl phenyl carbonate, butyl phenyl carbonate and hexyl phenyl carbonate, methyl o-cresyl carbonate, methyl p-cresyl carbonate, ethyl o-cresyl carbonate, ethyl p-cresyl carbonate, methyl or ethyl p-chlorophenyl carbonate. Particularly preferred alkyl aryl carbonates are methyl phenyl carbonate and ethyl phenyl carbonate. Very particular preference is given to methyl phenyl carbonate.

The diaryl carbonate to be purified also referred to as crude diaryl carbonate—preferably contains 10 to 90% by weight, more preferably 20 to 80% by weight and most preferably 40 to 80% by weight of diaryl carbonate, and 5 to 90% by weight, more preferably 5 to 60% by weight and most preferably 5 to 40% by weight of alkyl aryl carbonate, 1 to 90% by weight, more preferably 1 to 50% by weight and most preferably 1 to 30% by weight of aromatic hydroxyl compound, 0 to 5% by weight, more preferably 0 to 2% by weight and most preferably 0 to 0.5% by weight of high-boiling secondary components, 0 to 5% by weight, more preferably 0.0001 to 2% by weight and most preferably 0.0001 to 1% by weight of medium-boiling secondary components and 0.01 to 10% by weight, more preferably 0.1 to 5% by weight and most preferably 1 to 5% by weight of catalyst, where the sum of all components mentioned above in the diaryl carbonate to be purified adds up to 100% by weight. The percentages by weight are based in each case on the total weight of the crude diaryl carbonate to be purified.

High-boiling secondary components often also referred to as high boilers—in the context of the invention are those whose boiling point is above that of the diaryl carbonate. Medium-boiling components—often also referred to as intermediate boilers—in the context of the invention are those whose boiling point is between that of the diaryl carbonate and that of the alkyl aryl carbonate which is formed as an intermediate during the preparation of the diaryl carbonate.

The process according to the invention can provide preferably diaryl carbonates with a purity of, i.e. a content of pure diaryl carbonate of, 99 to 100% by weight, more preferably 99.5 to 100% by weight and most preferably 99.9 to 100% by weight, based on the total weight of the purified diaryl carbonate.

The diaryl carbonate withdrawn in the sidestream of the first distillation column can be withdrawn from the first distillation column in liquid or vaporous form. The diaryl carbonate withdrawn in the sidestream of the first distillation column is preferably withdrawn in vaporous form from the first distillation column. In certain preferred embodiments, however, the liquid withdrawal of the diaryl carbonate in the sidestream may be preferred, especially for construction reasons.

The first distillation column has at least two sections, i.e. a rectifying section in the upper part of the column and a stripping section in the lower part of the column. The rectifying section of the first distillation column can preferably be divided into a lower rectifying section and an upper rectifying section. In addition, the stripping section of the first distillation column can preferably be divided into a lower stripping section and an upper stripping section.

In total, the first distillation column preferably has a total separating performance of 3 to 160 theoretical plates, more preferably of 10 to 90 theoretical plates, most preferably of 13 to 50 theoretical plates. The upper rectifying section preferably has a separating performance of 0 to 40 theoretical plates, more preferably 1 to 20 theoretical plates, most preferably 1 to 10 theoretical plates, the lower rectifying section preferably 1 to 40 theoretical plates, more preferably 5 to 20 theoretical plates and most preferably 5 to 15 theoretical plates, the upper stripping section preferably 1 to 40 theoretical plates, more preferably 2 to 30 theoretical plates and most preferably 5 to 20 theoretical plates, and the lower stripping section preferably 1 to 40 theoretical plates, more preferably 2 to 20 theoretical plates and most preferably 2 to 15 theoretical plates.

The evaporation is effected preferably within a temperature range of 100 to 300° C., preferentially of 150 to 240° C. and more preferably of 180 to 230° C., in the bottom of the column. The vapors can be condensed at the top of the column in one or more stages, preferably one or two stages, within a temperature range of preferably 40 to 250° C., preferentially 50 to 200° C. and more preferably 60 to 180° C.

The bottom product of the first distillation column has a residual content of diaryl carbonate of below 95% by weight, preferably below 90% by weight and more preferably below 75% by weight. To avoid catalyst losses, the bottom product of the first distillation column can be recycled back into the transesterification of the dialkyl carbonate and the aromatic hydroxyl compound, preferably to an extent of at least 50%, more preferably to an extent of at least 80% and most preferably to an extent of at least 90%. The remaining portion of the bottom product of the first distillation column can be sent to a further refinery step, referred to hereinafter as residue concentration, for the purpose of concentrating the residue and partly recovering the diaryl carbonate still present in the bottom product of the first distillation column. The diaryl carbonate recovered in the residue concentration can, in a particular embodiment of the process, be fed back to the first distillation column in liquid or vaporous form, preferably in vaporous form. The concentrated residue from the residue concentration can either be discharged from the process or be sent to a further refinery step for the purpose of recovering the catalyst. This allows both losses of expensive catalysts and losses of desired diaryl carbonate to be prevented and hence the process according to the invention additionally to be operated more economically.

The first distillation column is preferably operated at a top pressure of 1 to 1000 mbar (absolute), more preferably of 1 to 100 mbar (absolute) and most preferably of 5 to 50 mbar (absolute).

In preferred embodiments of the process according to the invention, lines and units which conduct mixtures which have a melting point of more than 30° C., preferably more than 40° C., are heated to temperatures above this melting point, preferably to temperatures of more than 1° C. above this melting point, more preferably to temperatures of more than 5° C. above this melting point. This prevents precipitations of solids within these lines and units and considerably eases the restart of the corresponding equipment after shutdowns.

The process according to the invention is described by way of example with reference to FIGS. 1 to 5b. The figures serve for illustrative explanation of the invention and should not be interpreted as a restriction.

In FIGS. 1.1 to 5b:

$K_3$ first diaryl carbonate distillation column with sidestream withdrawal $K_3C_{1-N}$ one- or multistage top condenser (series and/or parallel connection)

$K_3E_{1-N}$ one- or multistage evaporator for bottom product (series and/or parallel connection)

$K_3VT_1$ upper rectifying section $K_3VT_2$ lower rectifying section $K_3AT_1$ upper stripping section $K_3AT_2$ (lower) stripping section $K_3SC_{1-N}$ one-stage or multistage sidestream condenser (series and/or parallel connection)

$K_4$ sidestream column $K_4C_{1-N}$ one-stage or multistage top condenser of the sidestream column (series and/or parallel connection)

$K_4VT_1$ rectifying section of the sidestream column $K_4AT_1$ stripping section of the sidestream column $K_4E_{1-N}$ one-stage or multistage evaporator for bottom product of the sidestream column (series and/or parallel connection)

T dividing wall $K_3TLO$ rectifying section on the feed side of the dividing wall $K_3TLU$ stripping section on the feed side of the dividing wall $K_3TRO$ rectifying section on the withdrawal side of the dividing wall $K_3TRU$ stripping section on the withdrawal side of the dividing wall $K_3CS_{1-N}$ one or more column section(s) for condensation in the distillation or dividing wall column (series and/or parallel connection)

$K_3W_{1-N}$ one or more liquid coolers (series and/or parallel connection)

$K_3RA$ residue concentration $K_3E_{N+1}$ residue concentration in the form of an evaporator In addition, the following streams are named in FIGS. 1.1 to 5b:

1 crude diaryl carbonate
2 distillate of column $K_3$
3 bottom product of column $K_3$
4 additional sidestream of $K_3$ with intermediate boilers
5 purified liquid diaryl carbonate
6 vaporous sidestream of $K_3$
7 vapors at the top of sidestream column $K_4$
8 reflux of sidestream column $K_4$
9 bottom products of column $K_4$
10 vapors from $K_3$ for condensation in $K_3C_{1-N}$
11 reflux of column $K_3$
12 liquid from lower stripping section of $K_3$
13 vapor/liquid mixture from $K_3E_{1-N}$
14 liquid from rectifying section to $K_3TLO$ (special version of $K_3$ as dividing wall column)
15 liquid from rectifying section to $K_3TRO$ (special version of $K_3$ as dividing wall column)
16 vapor from stripping section to $K_3TLU$ (special version of $K_3$ as dividing wall column)
17 vapor from stripping section to $K_3TRU$ (special version of $K_3$ as dividing wall column)
18 uncondensed vapors and/or inerts to condensation $K_3C_{1-N}$
19 uncondensed vapors and/or inerts to condensation $K_4C_{1-N}$
20 diaryl carbonate-containing stream from $K_3RA$
21 substream from condensation section $K_3CS_{1-N}$ to the cooler $K_3W_{1-N}$
22 cooled condensate from $K_3W_{1-N}$ to the condensation section $K_3CS_{1-N}$
23 liquid from stripping section of the sidestream column $K_4$
24 catalyst-containing stream to the transesterification (substream from bottom $K_3$)
25 substream from bottom product of $K_3$ to $K_3RA$ or $K_3E_{N+1}$
26 stream from $K_3RA$ to the discharge or catalyst recovery In various preferred embodiments of the process according to the invention, the purification of the diaryl carbonate is carried out in a distillation column which has at least three sections. These at least three sections are at least one rectifying section and at least one stripping section, the stripping section being divided into a lower stripping section and an upper stripping section. More preferably, the distillation column with a rectifying section and a stripping section, the stripping section being divided into a lower stripping section and an upper stripping section, four sections, in which case the rectifying section is also divided into a lower rectifying section and an upper rectifying section.

Such a particularly preferred variant of a process according to the invention is shown by way of example in FIG. 1.1. The distillation column $K_3$ of this preferred embodiment has four sections, a lower stripping section ($K_3AT_7$) and an upper stripping section ($K_3AT_1$) and also a lower rectifying section ($K_3VT_2$) and an upper rectifying section ($K_3VT_1$). The crude diaryl carbonate (1) is fed to the column between the lower rectifying section $K_3VT_2$ and upper stripping section $K_3AT_1$.

The upper rectifying section preferably has a separating performance of 0 to 40 theoretical plates, more preferably 1 to 20 theoretical plates and most preferably 1 to 10 theoretical plates, the lower rectifying section preferably 1 to 40 theoretical plates, more preferably 5 to 20 theoretical plates and most preferably 5 to 15 theoretical plates, the upper stripping section preferably 1 to 40 theoretical plates, more preferably 2 to 30 theoretical plates and most preferably 5 to 20 theoretical plates, and the lower stripping section preferably 1 to 40 theoretical plates, more preferably 2 to 20 theoretical plates and most preferably 2 to 15 theoretical plates.

To achieve this separating performance of the sections, random packings or structured packings can be used. The random packings or structured packings to be used are those customary for distillations, as described, for example, in Ullmann's Encyclopädie der Technischen Chemie, 4th ed., vol. 2, p. 528 ff. Examples of random packings include Raschig rings or Pall rings and Novalox rings, Berl saddles, Intalex saddles or Torus saddles, and Interpack packings, and examples of structured packings include sheet metal and fabric packings (for example BX packings, Montz Pak, Mellapak, Melladur, Kerapak and CY packings) made of various materials, such as glass, stoneware, porcelain, stainless steel, plastic. Preference is given to random packings and structured packings which have a large surface area, good wetting and sufficient residence time of the liquid phase. These are, for example, Pall and Novolax rings, Berl saddles, BX packings, Montz Pak, Mellapak, Melladur, Kerapak and CY packings. Alternatively, column trays are also suitable, for example sieve trays, bubble-cap trays, valve trays, tunnel-cap trays. Preference is given to using random packings and structured packings, particular preference to using structured packings.

In the context of the invention, a section features a feedpoint and/or withdrawal point below and/or above this section. In the case of use of random packings and/or structured packings, a section may be divided into several parts when the section has more than 4, preferably more than 10 and more preferably more than 15 theoretical plates.

The distillation column additionally has a one-stage or multistage (N-stage) top condenser $K_3C_{1-N}$ and a one-stage or multistage (N-stage) evaporator $K_3E_{1-N}$ for the bottom product. In the case of condensation or evaporation in several apparatuses (condensers or evaporators), both parallel and/or series connections and combinations of parallel and series connection are possible.

The vapors can be condensed at the top of the distillation column in one or more stages, preferably one or two stages, within a temperature range of 40 to 250° C., preferably of 50 to 200° C. and more preferably of 60 to 180° C.

With regard to the condensation in the top condenser, different embodiments are conceivable. Suitable top condensers are, for example, tube bundle or plate heat exchangers. The ratio $d_1/D_1$ of diameter of the vapor Tine from the column to the condenser ($d_1$) relative to column diameter of the first distillation column ($D_1$) is preferably in the range of 0.2 to 1.0, more preferably in the range of 0.5 to 1. In a particularly preferred embodiment, the top condenser can be integrated into the distillation column, such that no vapor line is required between distillation column and top condenser. In this case, the $d_1/D_1$ ratio is 1. At the same time, the column cross section after entry into the top condenser can also be adjusted to the progress of condensation under some circumstances. Such preferred embodiments are shown in sections and by way of example in FIGS. 5a and 5b.

Figure 5A:
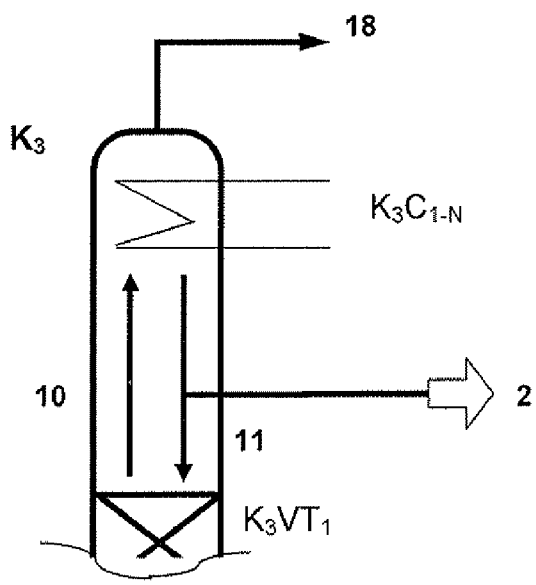
FIG. 5*a* is a process diagram of a section of the condensation at the top of a distillation or dividing wall column, the column diameter remaining unchanged in the region of the condensation in accordance with an embodiment of the present invention.
Figure 5B:
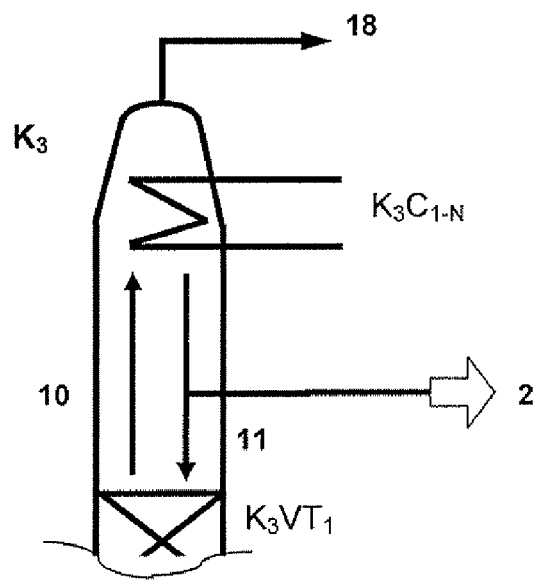
FIG. 5*b* is a process diagram of a section of the condensation at the top of a distillation or dividing wall column with a reduction in the column diameter in the direction of the top of the column in accordance with an embodiment of the present invention.

In the embodiment shown in FIG. 5a, the column diameter remains unchanged in the region of the condensation. The vapors (10) ascending out of the rectifying section, if present preferably the upper rectifying section $K_3VT_1$, are condensed in the integrated top condenser(s) $K_3C_{1-N}$. A portion of the condensate is introduced as reflux (11) back to the upper column section. The remaining portion of the condensate is discharged from the column as distillate (2). Inerts and/or uncondensed vapors (18) are withdrawn from the column at the top.

In some condenser types, it may be advantageous to make the column cross section variable. When the vapors to be condensed are conducted, for example, from the bottom upward, the amount of vapor decreases in the upward direction. By virtue of a reduction in the column diameter in the direction of the top of the column, the column cross section available for the vapor is adjusted to the amount of vapor decreasing in the upward direction. Such an embodiment is shown by way of example in FIG. 5b. In this case, the uncondensed vapors need not necessarily be withdrawn at the top. When, for example, a construction in which a plate bundle or tube bundle is inserted into the column from the top is selected, the withdrawal of the uncondensed vapors may also be disposed at the side.

A further preferred embodiment of a top condenser is shown in FIG. 4. In this embodiment, the vapors (10) ascending out of the rectifying section, if present preferably the upper rectifying section $K_3VT_1$, are condensed in one or more additional column section(s) ($K_3CS_{1-N}$) with a condensate cooled in an external circuit. The liquid emerging at the lower end of this column section is partly withdrawn (21) and sent to one or more external cooler(s) $K_3W_{1-N}$, which may be connected either in series or in parallel, to remove the heat of condensation obtained. The remaining liquid is either discharged as distillate (2) or introduced as reflux (11) to the rectifying section, if present preferably to the upper rectifying section $K_3VT_1$. After the cooling, the liquid (22) is fed back to the distillation column above the additional column section (s) $K_3CS_{1-N}$. Condensation in the column can take place on column trays, random packings or structured packings already described above. The uncondensed vapors or inerts (18) are withdrawn above the column section(s) $K_3CS_{1-N}$.

The liquid 12 effluxing from the lower stripping section $K_3AT_2$ in the illustrative diagram in FIG. 1.1 is concentrated by evaporation in a one-stage or multistage (N-stage) evaporation, and the vapors of the liquid/liquid mixture (13) obtained are sent back to the lower stripping section $K_3AT_2$. The evaporation is effected preferably within a temperature range of 150 to 300° C., preferably of 160 to 240° C. and more preferably of 180 to 230° C. in the bottom of the column. The temperature at the top of the column is preferably 40 to 250° C., preferably 50 to 200° C. and more preferably 60 to 180° C. A bottom product (3) is obtained with a residual content of diaryl carbonate of below 95% by weight, preferably below 90% by weight and more preferably below 75% by weight.

The purified diaryl carbonate is preferably withdrawn as a vaporous substream (6) above the lower stripping section $K_3AT_2$ and then condensed in a one-stage or multistage (N-stage) condenser $K_3SC_{1-N}$ and removed as liquid 5.

The heat of condensation obtained in the course of condensation in the condenser(s) $K_3SC_{1-N}$ can preferably be used for steam generation or for heating other process steps, for example those in the preparation of diaryl carbonates.

The distillation column $K_3$ is operated preferably at a top pressure of 1 to 1000 mbar (absolute), more preferably of 1 to 100 mbar (absolute) and most preferably of 5 to 50 mbar (absolute). The reflux ratio is set such that the diaryl carbonate content in the distillate 10 is preferably less than 10% by weight, more preferably less than 5% by weight and most preferably less than 1% by weight, based on the total weight of the distillate. For this purpose, a reflux ratio of 0.2 to 5, more preferably 0.2 to 2 and most preferably of 0.3 to 1.6 is established, the reflux ratio in the context of the invention corresponding to the weight ratio of condensate recycled into the column to vapor withdrawn at the top of the column without recycled condensate.

When the crude diaryl carbonate comprises compounds having a boiling point between that of the diaryl carbonate and that of the alkyl aryl carbonate formed as a by-product during the preparation of the diaryl carbonate as an impurity, these compounds can, in accordance with the invention, be withdrawn from the first distillation column in a further sidestream 4.

As shown in FIG. 1.2, the bottom product of the first distillation column (3), to avoid catalyst losses, can be recycled (24) back into the transesterification of the dialkyl carbonate and the aromatic hydroxyl compound to prepare the diaryl carbonate to an extent of at least 50%, preferably at least 80% and more preferably at least 90%. The remaining portion (25) of the bottom product can be sent to a residue concentration ($K_3RA$) for the purpose of concentrating the residue and partly recovering the diaryl carbonate still present in the bottom product of the first distillation column. The diaryl carbonate (20) recovered in the residue concentration can be fed back to the first distillation column in liquid or vaporous form, preferably in vaporous form. The concentrated residue (26) can either be discharged from the process or be sent to a further refinery step for the purpose of recovering the catalyst.

In a very particularly preferred embodiment which is shown by way of example in FIG. 1.3, the residue (25) is concentrated by means of an evaporator ($K_3E_{N+1}$). The vapors (20) obtained in the evaporation are passed into the bottom of the first distillation column ($K_3$). In this case too, the concentrated residue (26) can either be discharged from the process or be sent to a further refinery step for the purpose of recovering the catalyst.

In the case of discharge of the concentrated residue (26), the loss of diaryl carbonate is less than 2%, preferably less than 1%, more preferably less than 0.5%, based on the amounts of purified diaryl carbonate.

The above-described refining of the bottom product of the first distillation column can optionally also be carried out in all further embodiments presented below.

In a particularly preferred embodiment of the process according to the invention, the diaryl carbonate withdrawn in the sidestream of the first distillation column is purified in at least one distillation column, preferably in one, further distillation column. Such a further distillation column for purification of the diaryl carbonate withdrawn in the sidestream of the first distillation column is also referred to hereinafter as sidestream column for short.

In a particularly preferred variant of this preferred embodiment, this further distillation column (sidestream column) is designed without a stripping section. Such a particularly preferred variant of this preferred embodiment is shown by way of example in FIG. 2.1.

In this particularly preferred variant, the diaryl carbonate is purified in a distillation column $K_3$—as already described in connection with FIG. 1.1—and an additional sidestream column $K_4$. The vaporous sidestream 6 is fed to the sidestream column $K_4$, preferably to the lower part thereof. Compared to the version in FIG. 1.1, the distillation column $K_3$ has an additional feed 9 above the lower stripping section $K_3AT_2$, through which the liquid bottom product is recycled from the sidestream column $K_4$ back into $K_3$.

The sidestream column $K_4$ preferably has at least one section. More preferably, as shown in FIG. 2.1, it is operated as a pure rectifying section $K_4VT_1$ and possesses preferably a separating performance of 1 to 50 theoretical plates, more preferably of 2 to 30 theoretical plates and most preferably of 5 to 20 theoretical plates.

The sidestream column $K_4$ is operated at a top pressure of 1 to 1000 mbar (absolute), more preferably of 1 to 100 mbar (absolute) and most preferably of 5 to 50 mbar (absolute). In the sidestream column, preferably a reflux ratio of 0.1 to 10, more preferably of 0.2 to 5 and most preferably of 0.2 to 2 is established.

The condensation of the vapors (7) at the top of the sidestream column $K_4$ can be effected in one or more stages in a top condenser $K_4C_{1-N}$. It is preferably effected in one or two stages within a temperature range of 70 to 250° C., more preferably of 90 to 230° C. and most preferably of 90 to 210° C. The waste heat obtained in the condensation can preferably be used to generate steam or to heat other process parts, for example those in the preparation of diaryl carbonates. The condensate obtained in the condensation is partly reintroduced to the sidestream column as reflux (8). The remaining portion of the condensate is withdrawn as distillate (5) (purified diaryl carbonate). Inerts and/or uncondensed vapors (19) are discharged.

With regard to the condensation in the condenser $K_4C_{1-N}$, the same embodiments as already described above for the condensation at the top of the distillation column $K_3$ ($K_3C_{1-N}$) are suitable.

In a further particularly preferred variant of the particularly preferred embodiment of the process according to the invention using a further distillation column (sidestream column), this her distillation column (sidestream column) is configured both with at least one rectifying section and with at least one stripping section. Such a particularly preferred variant of this preferred embodiment is shown by way of example in FIG. 2.3.

The sidestream column $K_4$ shown in FIG. 2.3 has both a stripping section $K_4AT_1$ and a rectifying section $K_4AT_2$. The vaporous sidestream 6 of the first distillation column $K_3$ can first be condensed in a one-stage or multistage sidestream condenser $K_3SC_{1-N}$ and then be sent to the sidestream column $K_4$. The sidestream column $K_4$ is operated at a top pressure of 1 to 1000 mbar (absolute), preferably 1 to 100 mbar (absolute) and more preferably 5 to 50 mbar (absolute). This gives rise to a temperature in the bottom of 150 to 300° C., preferably of 160 to 240° C. and more preferably 180 to 230° C.

The sidestream column $K_4$ according to FIG. 2.3 has an overall separating performance of 5 to 100 plates, preferably 10 to 80 plates and more preferably 30 to 80 plates, in which case the rectifying section thereof has a separating performance of 1 to 99 plates, preferably of 1 to 79 plates and more preferably of 2 to 79 plates. The sidestream column $K_4$ is operated at a reflux ratio of 0.5 to 20, preferably 1 to 10 and more preferably 1 to 5.

The vapors (7) can be condensed at the top of the sidestream column $K_4$ in one or more stages in a top condenser $K_4C_{1-N}$. They are preferably condensed in one or two stages within a temperature range of 70 to 250° C., more preferably of 90 to 230° C. and most preferably of 90 to 210° C. The waste heat obtained in the condensation can preferably be used to generate steam or to heat other process parts, for example those in the preparation of diaryl carbonates. The condensate obtained in the condensation is partly reintroduced to the sidestream column as reflux (8). The remaining portion of the condensate is withdrawn as distillate (5) (purified diaryl carbonate). Uncondensed vapors (19) are discharged.

The liquid (23) effluxing from the stripping section $K_4AT_1$ of the sidestream column can likewise be evaporated in one or more stages in an evaporator $K_4E_{1-N}$.

The bottom product (9) of sidestream column $K_4$ can subsequently be discharged completely or partly from the process and/or be sent completely or partly back to the distillation column $K_3$.

The above-described particularly preferred embodiment of the process according to the invention using a sidestream column is suitable especially for the purification of diaryl carbonates with increased demands regarding their quality. Such increased demands may lie, for example, in a reduced proportion of high-boiling secondary components, in which case their proportion in the diaryl carbonate can be reduced compared to the process with only one distillation column by 10 to 100% by weight, preferably 20 to 90% by weight and more preferably 25 to 80% by weight.

In a particularly preferred embodiment of the process according to the invention, the further distillation column is integrated into the first distillation column. In the case of the particularly preferred variant that the further distillation column is configured without a stripping section, the rectifying section of this further column is integrated into the first distillation column ($K_3$). Such a particularly preferred variant of this preferred embodiment is shown by way of example in FIG. 2.2. In this case, some of the vapors (6) coming from the lower stripping section of the first distillation column ($K_3AT_2$) pass into an integrated rectifying section ($K_4VT_1$), in order to reduce the content of high boilers. The vapors (7) emerging at the top of this integrated sidestream column are condensed in the external condenser(s) $K_4C_{1-N}$ and recycled partly as reflux (8) back to the top of the integrated sidestream column. The remaining portion of the condensate is withdrawn as distillate (5) (purified diaryl carbonate). Uncondensed vapors (19) are discharged.

In a further particularly preferred embodiment of the process according to the invention, the first distillation column is configured as a dividing wall column.

Dividing wall columns are likewise suitable for separating a mixture into three fractions, i.e. top product, bottom product and sidestream with high purity. The dividing wall column has a generally vertical dividing wall which divides the feed side from the withdrawal side for the sidestream from one another. The dividing wall is preferably not continuous over the entire length of the column. Usually, there is also a rectifying section above the dividing wall and a stripping section below the dividing wall. In the region of the dividing wall, both on the feed side and on the withdrawal side for the sidestream, there are preferably at least 2 sections. On the feed side, an upper section serves to reduce the high boilers present in the feed and a lower section to reduce the low boilers present in the feed. On the withdrawal side for the sidestream, there is likewise an upper section above the withdrawal, which serves to reduce the low boilers from the rectifying section. A lower section arranged below the withdrawal serves to reduce high boilers which come from the stripping section below the dividing wall.

The division of the liquid effluxing from the rectifying section is guided by the requirements on the specific separating task and can be influenced by construction measures and control technology measures. The same applies to the vapor stream coming from the stripping section.

Dividing wall columns are known to those skilled in the art and are described, for example, in German Patent Publication Nos. DE-A 33 02 525 or DE-A 199 14 966, the entire contents of each of which is hereby incorporated herein by reference.

The dividing wall column preferably has, in addition to at least one rectifying section in the upper part of the column and at least one stripping section in the lower part of the column, in each case an upper section and lower section on the feed side of the dividing wall and on the withdrawal side of the dividing wall, feed and withdrawal each being effected between the upper section and lower section.

In particularly preferred embodiments of the process according to the invention, the rectifying section of the dividing wall column has two sections, i.e. a lower rectifying section and an upper rectifying section.

In very particularly preferred embodiments of the process according to the invention, the dividing wall column has at least seven sections, including at least one stripping section in the lower part of the column, in each case an upper section and lower section on the feed side of the dividing wall and on the withdrawal side of the dividing wall, and an upper and lower rectifying section in the upper part of the column.

The dividing wall in such a dividing wall column is preferably arranged in the longitudinal direction of the column. It prevents mass transfer between feed side and withdrawal side both on the vapor side and on the liquid side.

An illustrative embodiment of the process according to the invention with a dividing wall column having seven sections is shown by way of example in FIG. 3.1. The dividing wall column $K_3$ in FIG. 3.1 has a stripping section $K_3AT_1$ in the lower part of the column $K_3$, in each case an upper section $K_3TLO$ and a lower section $K_3TLU$ on the feed side of the dividing wall T, and an upper section $K_3TRO$ and lower section $K_3TRU$ on the withdrawal side of the dividing wall T, and also an upper rectifying section $K_3VT_1$ and lower rectifying section $K_3VT_2$ in the upper part of the column. The crude diaryl carbonate (1) is fed to the column between the upper section $K_3TLO$ and the lower section $K_3TLU$ on the feed side of the dividing wall T of column; the purified diaryl carbonate (5) is withdrawn from the column between the upper section $K_3TRO$ and the lower section $K_3TRU$ on the withdrawal side of the dividing wall T.

The upper section $K_3TLO$ disposed on the feed side of the dividing wall serves for the removal of high boilers which are present in the feed. The lower section $K_3TLU$ on the feed side of the dividing wall serves for the removal of low boilers which are present in the crude diaryl carbonate (1). The upper section $K_3TRO$ disposed on the withdrawal side of the dividing wall serves to remove low boilers which are present in the liquid stream (15) emerging from the rectifying section $K_3VT_2$ in the upper part of the column. The lower section of the withdrawal side $K_3TRU$ serves for removal of high boilers which are present in the vapor stream (17) emerging from the stripping section $K_3AT_1$.

The purified diaryl carbonate can be withdrawn on the withdrawal side of the dividing wall in liquid or vaporous form. In the column design, the type of removal can sometimes significantly influence the arrangement of the dividing wall within the column. The dividing wall can be arranged in the column in each case shifted to the withdrawal side or to the feed side and hence reduce or increase the cross section of the particular side compared to the other. In the case of vaporous withdrawal of the purified diaryl carbonate on the withdrawal side of the dividing wall, the cross section of the withdrawal side of the column is preferably greater than the cross section of the feed side, i.e. more vapor passes from the stripping section to the withdrawal side. In the case of liquid withdrawal of the purified diaryl carbonate on the withdrawal side of the dividing wall, the cross section of the feed side of the column is preferably identical to the cross section of the withdrawal side.

In the case of liquid withdrawal of the purified diaryl carbonate, which is shown by way of example in FIG. 3.1, 10 to 90%, preferably 20 to 90%, more preferably 50 to 85%, of the liquid effluxing from the section $K_3TRO$ of the withdrawal side is withdrawn as sidestream 5. The remaining liquid is fed to the lower section $K_3TRU$ of the withdrawal side. The liquid effluxing from the rectifying section $K_3VT_2$ is introduced (14) to the feed side of the dividing wall, i.e. above $K_3TLO$, to an extent of 5 to 50%, preferably to an extent of 10 to 50% and more preferably to an extent of 10 to 40%. The remaining liquid is introduced (15) at the upper end of the withdrawal side of the dividing wall, i.e. to $K_3TRO$. The vapor ascending out of the stripping section $K_3AT_1$ is fed (16) to the feed side of the dividing wall to an extent of 5 to 90%, preferably to an extent of 10 to 80% and more preferably to an extent of 20 to 75%.

In the case of vaporous withdrawal of the purified diaryl carbonate, which is shown by way of example in FIG. 3.2, 10 to 90%, preferably 20 to 90%, more preferably 50 to 85%, of the vapor emerging from the lower section $K_3TRU$ of the withdrawal side is withdrawn as sidestream (6). The remaining vapor is fed to the upper section $K_3TRO$ of the withdrawal side. The liquid effluxing from the rectifying section $K_3VT_2$ is introduced (14) to the feed side of the dividing wall, i.e. above $K_3TLO$, to an extent of 5 to 90%, preferably to an extent of 10 to 80% and more preferably to an extent of 20 to 60%. The remaining liquid is introduced (15) at the upper end of the withdrawal side of the dividing wall, i.e. to $K_3TRO$. The vapor ascending out of the stripping section $K_3AT_1$ is fed (16) to the feed side of the dividing wall to an extent of 5 to 90%, preferably to an extent of 10 to 80% and more preferably to an extent of 20 to 60%. In the case of the vaporous withdrawal, the sidestream (6) withdrawn in vaporous form is preferably condensed in one or more sidestream condenser(s) $K_3SC_{1-N}$ and removed as liquid diaryl carbonate stream (5).

The upper rectifying section of such a dividing wall column preferably has a separating performance of 0 to 40 theoretical plates, more preferably 1 to 20 theoretical plates and most preferably 1 to 10 theoretical plates, the lower rectifying section preferably 1 to 40 theoretical plates, more preferably 5 to 20 theoretical plates and most preferably 5 to 15 theoretical plates, and the stripping section preferably 1 to 40 theoretical plates, more preferably 2 to 20 theoretical plates and most preferably 2 to 15 theoretical plates. The upper section $K_3TLO$ and the lower section $K_3TLU$ on the feed side of the dividing wall and the upper section $K_3TRO$ and lower section $K_3TRU$ on the withdrawal side of the dividing wall preferably each have a separating performance of 1 to 40 theoretical plates, more preferably 2 to 20 theoretical plates and most preferably 5 to 20 theoretical plates.

To achieve this separating performance of the sections, random packings or structured packings can be used. The random packings or structured packings to be used are those customary for distillations, as described, for example, in Ullmann's Encyclopädie der Technischen Chemie, 4th ed., vol. 2, p. 528 ff. Examples of random packings include Raschig rings or Pall rings and Novalox rings, Berl saddles, Intalex saddles or Torus saddles, and Interpack packings, and examples of structured packings include sheet metal and fabric packings (for example BX packings, Montz Pak, Mellapak, Melladur, Kerapak and CY packings) made of various materials, such as glass, stoneware, porcelain, stainless steel, plastic. Preference is given to random packings and structured packings which have a large surface area, good wetting and sufficient residence time of the liquid phase. These are, for example, Pall and Novolax rings, Berl saddles, BX packings, Montz Pak, Mellapak, Melladur, Kerapak and CY packings. Alternatively, column trays are also suitable, for example sieve trays, bubble-cap trays, valve trays, tunnel-cap trays. Preference is given to using random packings and structured packings, particular preference to using structured packings.

The dividing wall column additionally has a one-stage or multistage N-stage) top condenser $K_3C_{1-N}$ and a one-stage or multistage (N-stage) evaporator $K_3E_{1-N}$ for the bottom product.

The vapors can be condensed at the top of the dividing wall column in one or more stages, preferably one or two stages, within a temperature range of 40 to 250° C., preferably of 50 to 200° C. and more preferably of 60 to 180° C. With regard to the condensation in the top condenser, the different embodiments of the condensers already specified above for the distillation columns are possible.

The liquid (12) effluxing from the stripping section $K_3AT_1$ is concentrated by evaporation in a one-stage or multistage (N-stage) evaporation, and the vapors of the liquid/liquid mixture (13) obtained are sent back to the lower stripping section $K_3AT_1$. The evaporation is effected preferably within a temperature range of 100 to 250° C., preferably of 150 to 240° C. and more preferably of 180 to 220° C.

The dividing wall column is operated at a top pressure of 1 to 1000 mbar (absolute), more preferably of 1 to 100 mbar (absolute) and most preferably of 5 to 50 mbar (absolute). The reflux ratio is adjusted such that the diaryl carbonate content in the distillate 10 is preferably less than 10% by weight, more preferably less than 5% by weight and most preferably less than 1% by weight, based on the total weight of the distillate. For this purpose, a reflux ratio of preferably 0.2 to 5, more preferably 0.2 to 2 and most preferably of 0.3 to 1.6 is established, the reflux ratio in the context of the invention corresponding to the weight ratio of condensate recycled into the column relative to vapor withdrawn at the top of the column without recycled condensate.

When the diaryl carbonate to be purified comprises compounds having a boiling point between that of the diaryl carbonate and the alkyl aryl carbonate formed as an intermediate during the preparation of the diaryl carbonate as an impurity, this impurity can be removed in accordance with the invention in a further sidestream 4 of the dividing wall column.

The invention will now be described in further detail with reference to the following non-limiting examples.

EXAMPLES

The following abbreviations with the corresponding definitions are used hereinafter:
DMC: dimethyl carbonate
MPC: methyl phenyl carbonate
DPC: diphenyl carbonate
Ti(PhO)$_4$: titanium tetraphenoxide
Salol: phenyl salicylate
DPE: diphenyl ether Example 1

DPC Purification in a First Distillation Column (Fine Distillation) with Sidestream Column According to FIG. 2.1

A two-stage transesterification affords 224.4 kg/h of a DPC-containing stream comprising 63.8/22.7/10.3/0.4/2.7/ 0.08% by weight of DPC/MPC/phenol/DMC/Ti(PhO)$_4$/salol. This stream is worked up in a distillative refinery composed of a first distillation column (fine distillation) with vaporous sidestream withdrawal ($K_3$) and a sidestream column ($K_4$) according to FIG. 2.1. In addition, 1.3 kg/h of a vaporous mixture from a residue concentration comprising 99.6% by weight of DPC are fed in at the bottom of the column $K_3$.

The fine distillation ($K_3$) consists of four sections, an upper rectifying section with 2 theoretical plates, a lower rectifying section with 12 theoretical plates, an upper stripping section with 10 theoretical plates and a lower stripping section with 9 theoretical plates. The condensation of the vapors emerging at the top of the column in the top condenser ($K_3C_1$) and the partial evaporation of the liquid effluxing from the lower stripping section ($K_3AT_2$) in the evaporator $K_3E_1$ for the bottom product are each effected in one stage.

The column is operated at a top pressure of 15 mbar and a reflux ratio of 0.7.

This affords, as distillate (2), a stream comprising 69.9/28.3/1.2/0.5% by weight of MPC/phenol/DMC/DPE. Below the upper rectifying section $K_3VT_1$, 0.02 kg/h of liquid are withdrawn for the purpose of discharge of high boilers in the sidestream (4). In addition, below the upper rectifying section $K_3VT_1$, 192.8 kg/h of a vaporous sidestream (6) comprising 99.9% by weight of DPC are withdrawn. The bottom product (3) obtained is 20.8 kg/h of a mixture comprising 69.8/29.6/0.5% by weight of DPC/Ti(PhO)$_4$/salol. A substream of the bottom product, whose amount corresponds to 10% based on the total amount of the bottom product (3), is sent to a residue concentration ($K_3RA$), consisting of a thin-film evaporator ($K_3E_2$). The remaining bottom product (24) is recycled back to the two-stage transesterification to prepare the DPC-containing stream (1). This reduces the catalyst loss by 90%.

The vaporous sidestream (6) is sent to a sidestream column $K_4$. This possesses only a rectifying section $K_4VT_1$ with 9 theoretical plates.

The sidestream column $K_4$ is operated under the same conditions as the fine distillation in the first distillation column $K_3$ and at a reflux ratio of 0.5.

The vapors (7) emerging at the top of the sidestream column $K_4$ are condensed in a two-stage condensation in the condensers $K_4C_{1-N}$, the heat of condensation being used either to generate steam or to heat other process parts in the DPC preparation.

This affords a distillate comprising 99.93% by weight of DPC and only 600 ppm of salol. The liquid 9 effluxing at the top of the sidestream column is sent to the fine distillation in the first distillation column $K_3$ above the lower stripping section $K_3AT_2$.

Example 2

DPC Purification in a Dividing Wall Column with Liquid Sidestream Withdrawal

For this example, a dividing wall column according to FIG. 3.1 is used. The dividing wall column $K_3$ consists of a rectifying section with 2 sections. The upper section $K_3VT_1$ has a separating performance of 2 theoretical plates, the section $K_3VT_2$ below it a separating performance of 12 theoretical plates. Below the upper rectifying section $K_3VT_1$ there is the possibility of withdrawing a liquid stream (4) to discharge diphenyl ether.

Below the rectifying section, the column is partitioned by a vertical dividing wall T. On the withdrawal side and feed side of this dividing wall are in each case disposed at least 2 sections. The feed (1) is introduced on the feed side of the dividing wall. A liquid withdrawal of the purified diphenyl carbonate (5) is effected on the withdrawal side.

The upper section $K_3TLO$ disposed on the feed side of the dividing wall serves for the removal of high boilers which are present in the feed (1). The lower section of the feed side $K_3TLU$ serves for the removal of low boilers which are present in the feed (1). The upper section $K_3TRO$ disposed on the withdrawal side of the dividing wall serves for the removal of low boilers which are present in the liquid stream (15) emerging from the rectifying section. The lower section of the withdrawal side $K_3TRU$ serves for the removal of high boilers which are present in the vapor stream (17) emerging from the stripping section.

The stripping section $K_3AT_1$ has a separating performance of 14 theoretical plates and serves for the concentration of the high boilers.

The vapor (10) emerging from the rectifying section is condensed in a condenser $K_3C_{1-N}$ and introduced partly as reflux (11) back to the column. The liquid (12) effluxing from the stripping section is evaporated partly in an evaporator $K_3E_{1-N}$.

The column is operated at a top pressure of 15 mbar.

The feed rate (1) to the column $K_3$ is 236.6 kg/h. Present therein are 62.8/24.2/9.8/0.4/0.1/0.0312.6% by weight of DPC/MPC/phenol/DMC/DPE/salol/Ti(PhO)$_4$. The distillate (2) obtained is 81.8 kg/h of a mixture comprising 69.9/28.4/1.15/0.05/0.5% by weight of MPC/phenol/DMC/DPC/DPE. To discharge the DPE, 0.2 kg/h are withdrawn from the rectifying section as sidestream (4) comprising 61.3/33-5/0.9% by weight of DPC/MPC/DPE. The bottom product (3) obtained is 20.6 kg/h of a mixture of 69.7/29.8/0.41% by weight of DPC/Ti(PhO)$_4$/salol.

The diphenyl carbonate withdrawn in the sidestream (5) (134 kg/h) has a purity of 99.97% by weight and contains only 280 ppm of salol.

The liquid effluxing from the rectifying section is introduced to the feed side of the dividing wall, i.e. above $K_3TLO$, to an extent of 25%, and to the withdrawal side of the dividing wall, i.e. to $K_3TRO$, to an extent of 75%. The vapor ascending out of the stripping section $K_3AT_1$ is divided in equal parts between the feed side and withdrawal side of the dividing wall.

Example 3

DPC Purification in a Dividing Wall Column with Vaporous Sidestream Withdrawal

For this example, a dividing wall column according to FIG. 3.2 is used. The dividing wall column $K_3$ consists of a rectifying section with 2 sections. The upper section $K_3VT_1$ has a separating performance of 2 theoretical plates, the section $K_3VT_2$ below it a separating performance of 13 theoretical plates. Below the upper rectifying section $K_3VT_1$, there is the possibility of withdrawing a liquid stream (4) to discharge diphenyl ether.

Below the rectifying section, the column is partitioned by a vertical dividing wall T. On the feed side and the withdrawal side of this dividing wall are in each case disposed at least 2 sections. On the feed side of the dividing wall, the feed (1) is introduced. On the withdrawal side, there is a vaporous withdrawal of the purified diphenyl carbonate (6).

The upper section $K_3TLO$ disposed on the feed side of the dividing wall serves for the removal of high boilers which are present in the feed 1. The lower section of the feed side $K_3TLU$ serves for the removal of low boilers which are present in the feed 1. The upper section $K_3TRO$ disposed on the withdrawal side of the dividing wall serves for the removal of low boilers which are present in the liquid stream 15 emerging from the rectifying section. The lower section of the withdrawal side $K_3TRU$ serves for the removal of high boilers which are present in the vapor stream (17) emerging from the stripping section.

The stripping section $K_3AT_1$ has a separating performance of 14 theoretical plates and serves for concentration of the high boilers.

The vapor (10) emerging from the rectifying section is condensed in a condenser $K_3C_{1-N}$ and is introduced back to the column partly as reflux (11). The liquid (12) effluxing from the stripping section is partly evaporated in an evaporator $K_3E_{1-N}$.

The column is operated at a top pressure of 15 mbar.

To the column $K_3$ are fed 236.6 kg/h comprising 62.8/24.2/9.8/0.4/0.1/0.03/2.6% by weight of DPC/MPC/phenol/DMC/DPE/salol/Ti(PhO)$_4$ as feed (1). The distillate (2) obtained is 81.8 kg/h comprising 69.8/28.4/1.16/0.1/0.5% by weight of MPC/phenol/DMC/DPC/DPE. To discharge the DPE, 0.2 kg/h is withdrawn from the rectifying section as sidestream (4) comprising 68.3/27.1/0.7% by weight of DPC/MPC/DPE. The bottom product 3 obtained is 20.6 kg/h of a mixture of 69.7/29.8/0.41% by weight of DPC/Ti(PhO)$_4$/salol.

The diphenyl carbonate (5) which is withdrawn in the sidestream and subsequently condensed has a purity of 99.97% by weight and contains only 290 ppm of salol.

The liquid effluxing from the rectifying section is introduced to an extent of 25% to the feed side of the dividing wall, i.e. above $K_3TLO$, and to an extent of 75% to the withdrawal side of the dividing wall, i.e. to $K_3TRO$. The vapor ascending out of the stripping section $K_3AT_1$ is divided between the feed side of the dividing wall to an extent of 25% and the withdrawal side of the dividing wall to an extent of 75%.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process comprising:

transesterifying (i) a dialkyl carbonate of the general formula (II):

(II)

wherein $R^1$ and $R^2$ each independently represents a substituent selected from the group consisting of linear or branched, optionally substituted $C_1$-$C_{34}$-alkyl groups, and (ii) an aromatic hydroxyl compound of the general formula (III):

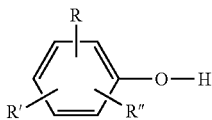
(III)

wherein R, R' and R" each independantly represents a substituent selected from the group consisting of hydrogen, linear or branched, optionally substituted $C_1$-$C_{34}$-alkyl groups, a $C_1$-$C_{34}$-alkoxy groups, $C_5$-$C_{34}$-cycloalkyl groups, $C_7$-$C_{34}$-alkylaryl groups, $C_{6-34}$-aryl groups, halogen radicals, and —COO—R'" wherein each R'" independently represents a substituent selected from the group consisting of hydrogen, linear or branched $C_1$-$C_{34}$ alkyl, $C_1$-$C_{34}$-alkoxy, $C_5$-$C_{34}$-cycloalkyl, $C_7$-$C_{34}$-alkylaryl and $C_6$-$C_{34}$-aryl, in the presence of a transesterification catalyst to provide a diaryl carbonate product comprising the transesterification catalyst as an impurity, wherein the diaryl carbonate product comprises a diaryl carbonate of the general formula (I):

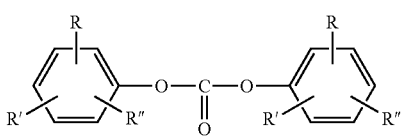
(I)

wherein each R, R' and R" is independently defined as above;

subjecting the diaryl carbonate product to distillation in a first dividing wall distillation column having an upper part and a lower part, wherein the upper part comprises a rectifying section and the lower part comprises a stripping section; and withdrawing a first sidestream from the first distillation column, wherein the first sidestream comprises a purified diaryl carbonate.

2. The process according to claim 1, further comprising subjecting the purified diaryl carbonate to an additional distillation in a second distillation column.

3. The process according to claim 2, wherein the second distillation column has no stripping section.

4. The process according to claim 2, wherein the second distillation column is integrated into the first distillation column.

5. The process according to claim 1, wherein the first sidestream is withdrawn from the first distillation column as a vapor.

6. The process according to claim 1, wherein the diaryl carbonate product further comprises an alkyl aryl carbonate transesterification by-product and an additional compound having a boiling point between that of the diaryl carbonate and the alkyl aryl carbonate; and the process further comprises withdrawing a second sidestream comprising the additional compound from the first distillation column.

7. The process according to claim 6, wherein the second sidestream is withdrawn from the first distillation column above the first sidestream.

8. The process according to claim 1, wherein the stripping section comprises an upper stripping section and a lower stripping section.

9. The process according to claim 1, wherein the rectifying section comprises an upper rectifying section and a lower rectifying section.

10. The process according to claim 1, wherein the dividing wall column comprises a dividing wall section having a dividing wall, a feed side and a withdrawal side; wherein the feed side comprises an upper feed side section and a lower feed side section, and the withdrawal side comprises an upper withdrawal side section and a lower withdrawal side section; and wherein the diaryl carbonate product is fed to the first distillation column between the upper and lower feed side sections and the first sidestream is withdrawn from the first distillation column between the upper and lower withdrawal sections.

11. The process according to claim 10, further comprising subjecting the purified diaryl carbonate to an additional distillation in a second distillation column.

12. The process according to claim 1, wherein the first distillation column has a diameter $D_1$ and further comprises a top condenser integrated into the first distillation column and a vapor line from the first distillation column to the top condenser, the vapor line having a diameter $d_1$, and wherein a ratio $d_1/D_1$ is 0.2 to 1.

13. The process according to claim 2, wherein the second distillation column has a diameter $D_2$ and further comprises a top condenser integrated into the second distillation column and a vapor line from the second distillation column to the top condenser, the vapor line having a diameter $d_2$, and wherein a ratio $d_2/D_2$ is 0.2 to 1.

14. The process according to claim 1, wherein a bottom product is withdrawn from a bottom of the first distillation column, and wherein the process further comprises recycling at least 50% of the bottom product back into the transesterification of the diallyl carbonate and the aromatic hydroxyl compound.

15. The process according to claim 14, wherein an unrecycled portion of the bottom product is concentrated and subjected to catalyst recovery.

16. The process according to claim 14, wherein the dividing wall column comprises a dividing wall section having a dividing wall, a feed side and a withdrawal side; wherein the feed side comprises an upper feed side section and a lower feed side section, and the withdrawal side comprises an upper withdrawal side section and a lower withdrawal side section; and wherein the diaryl carbonate product is fed to the first distillation column between the upper and lower feed side sections and the first sidestream is withdrawn from the first distillation column between the upper and lower withdrawal sections.

17. The process according to claim 16, further comprising subjecting the purified diaryl carbonate to an additional distillation in a second distillation column.

18. The process according to claim 14, wherein an unrecycled portion of the bottom product is concentrated and subjected to catalyst recovery.

* * * * *